United States Patent
Miresmailli et al.

(10) Patent No.: US 10,058,092 B2
(45) Date of Patent: Aug. 28, 2018

(54) APPARATUS AND METHOD FOR CONTROLLED RELEASE OF BOTANICAL FUMIGANT PESTICIDES

(71) Applicants: Saber Miresmailli, North Vancouver (CA); Helen D. Ojha, New York, NY (US); John W. Drury, Porrentruy (CH)

(72) Inventors: Saber Miresmailli, North Vancouver (CA); Helen D. Ojha, New York, NY (US); John W. Drury, Porrentruy (CH)

(73) Assignee: Sumatics, LLC, New York, NY (US)

( * ) Notice: Subject to any disclaimer, the term of this patent is extended or adjusted under 35 U.S.C. 154(b) by 532 days.

(21) Appl. No.: 13/861,890

(22) Filed: Apr. 12, 2013

(65) Prior Publication Data
US 2013/0295153 A1 Nov. 7, 2013

Related U.S. Application Data

(60) Provisional application No. 61/623,829, filed on Apr. 13, 2012.

(51) Int. Cl.
*A01N 25/18* (2006.01)
*A01M 1/20* (2006.01)
(Continued)

(52) U.S. Cl.
CPC .......... *A01N 25/18* (2013.01); *A01M 1/2022* (2013.01); *A01N 27/00* (2013.01); *A01N 35/06* (2013.01); *A01N 65/00* (2013.01); *A01N 65/22* (2013.01); *Y02A 50/336* (2018.01); *Y02A 50/338* (2018.01); *Y02A 50/339* (2018.01); *Y02A 50/34* (2018.01); *Y02A 50/344* (2018.01); *Y02A 50/348* (2018.01); *Y02A 50/351* (2018.01)

(58) Field of Classification Search
CPC .......................... A01M 2/2202; A01N 25/18
USPC ........................................................ 422/305
See application file for complete search history.

(56) References Cited

U.S. PATENT DOCUMENTS 3,482,929 A 12/1969 Gentil
3,851,648 A 12/1974 Brooke
(Continued)

FOREIGN PATENT DOCUMENTS

CN 101816315 A 9/2010
WO 1997047193 A1 12/1997
(Continued)

OTHER PUBLICATIONS

International Search Report and Declaration, International Application No. PCT/US13/36410, International Searching Authority, (dated Aug. 20, 2013).
(Continued)

*Primary Examiner* — Kevin Joyner
(74) *Attorney, Agent, or Firm* — Richard Blakely Glasgow

(57) ABSTRACT

A fumigant pesticide composition made up of a base formula and enhancement formula, which include botanical essential oil-based active ingredients and inert materials identified under the United States Environmental Protection Agency's approved list of minimum risk pesticides. The enhancement formula is effective to inhibit or enhance the release of the secondary metabolites of the essential oil-based active ingredients. An apparatus and method for the controlled release of the fumigant pesticide composition is also disclosed.

12 Claims, 8 Drawing Sheets

(51) Int. Cl.
*A01N 65/22* (2009.01)
*A01N 27/00* (2006.01)
*A01N 35/06* (2006.01)
*A01N 65/00* (2009.01)

(56) References Cited

U.S. PATENT DOCUMENTS

| | | | |
|---|---|---|---|
| 4,087,026 | A | 5/1978 | Petterson |
| 4,161,283 | A | 7/1979 | Hyman |
| 4,290,426 | A | 9/1981 | Luschen et al. |
| 4,605,165 | A | 8/1986 | Van Loveren et al. |
| 4,634,614 | A | 1/1987 | Holzner |
| 4,759,930 | A | 7/1988 | Granirer et al. |
| 4,809,912 | A | 3/1989 | Santini |
| 5,034,222 | A | 7/1991 | Kellett et al. |
| 5,591,435 | A | 1/1997 | Vaccarello-Dunkel et al. |
| 5,875,968 | A | 3/1999 | Miller et al. |
| 6,231,865 | B1 | 5/2001 | Hsu et al. |
| 6,338,296 | B1 | 1/2002 | Forsythe et al. |
| 6,352,210 | B1 | 3/2002 | Requejo |
| 6,531,163 | B1 | 3/2003 | Bessette et al. |
| 6,646,014 | B2 | 11/2003 | Watkins |
| 6,820,773 | B1 | 11/2004 | Orth |
| 7,109,240 | B2 | 9/2006 | Bessette et al. |
| 7,481,380 | B2 | 1/2009 | Kvietok et al. |
| 7,674,476 | B1 | 3/2010 | Schwertfeger et al. |
| 8,567,693 | B2 * | 10/2013 | Roreger ............ A01M 1/2055 239/53 |
| 2001/0006670 | A1 | 7/2001 | Karg |
| 2001/0041694 | A1 | 11/2001 | Clark et al. |
| 2001/0055628 | A1 | 12/2001 | Hsu et al. |
| 2002/0110576 | A1 | 8/2002 | Messina |
| 2002/0182353 | A1 | 12/2002 | Harlowe et al. |
| 2006/0034898 | A1 | 2/2006 | Amodt et al. |
| 2006/0175425 | A1 | 8/2006 | McGee et al. |
| 2007/0026765 | A1 | 2/2007 | Renn |
| 2007/0031463 | A1 | 2/2007 | Fotinos et al. |
| 2007/0098750 | A1 | 5/2007 | Bessette |
| 2008/0299168 | A1 | 12/2008 | Dadey et al. |
| 2010/0108778 | A1 | 5/2010 | Greenland |
| 2010/0120724 | A1 | 5/2010 | Bessette |
| 2011/0070322 | A1 | 3/2011 | Bessette et al. |
| 2011/0177149 | A1 | 7/2011 | Messina |
| 2012/0018527 | A1 | 1/2012 | Duddington et al. |
| 2012/0052109 | A1 | 3/2012 | Watkins et al. |

FOREIGN PATENT DOCUMENTS

| | | |
|---|---|---|
| WO | 2001010739 A1 | 2/2001 |
| WO | 2011142918 A1 | 11/2011 |

OTHER PUBLICATIONS

Apiguard, Six Reasons Why You Should Consider Treating With Apiguard, Draper's Super Bee Apiaries (2010).

Enan, E.E. (2005). Molecular response of *Drosophila melanogaster* tyramine receptor cascade to plant essential oils. Insect biochemistry and molecular biology, 35(4), 309-321.

Enan, E. (2001). Insecticidal activity of essential oils: octopaminergic sites of action. Comparative Biochemistry and Physiology Part C: Toxicology & Pharmacology, 130(3), 325-337.

Priestley, C.M., Williamson, E.M., Wafford, K.A., & Sattelle, D.B. (2009). Thymol, a constituent of thyme essential oil, is a positive allosteric modulator of human GABAA receptors and a homo-oligomeric GABA receptor from *Drosophila melanogaster*. British journal of pharmacology, 140(8), 1363-1372.

Cavanagh, H.M.A., & Wilkinson, J.M. (2002). Biological activities of lavender essential oil. Phytotherapy Research, 16(4), 301-308.

Isman, M.B., Miresmailli, S., & Machial, C. (2011). Commercial opportunities for pesticides based on plant essential oils in agriculture, industry and consumer products. Phytochemistry Reviews, 10(2), 197-204.

Volkov, A.G., Ranatunga, D.R.A. 2006. Plants as environmental biosensors. Plant Signaling and Behavior 1:105-115.

Miresmailli, S., Gries, R., Gries, G., Zamar, R.H. and Isman, M.B. 2012. Population density and feeding duration of cabbage looper larvae on tomato plants alter levels of plant volatile emission. Pest Management Science, 68: 101-107.

Schoonhoven, L.M., van Loon, J.J.A., Dicke, M. 2006. Insect-Plant Biology. New York: Oxford University Press. 421 p.

Bowen, A.W., Hall, D.E., MacGregor, K.B. 2002. Insect footsteps on leaves stimulate the accumulation of 4-aminobutyrate and can be visualized through increased chlorophyll fluorescence and superoxide production. Plant Physiology 129:1430-1434.

Kessler, A., Baldwin, I.T. 2001. Defensive function of herbivore-induced plant volatile emissions in nature. Science 291:2141-2144.

Carpenter, et al. Guidelines for Sensory Analysis in Food Products Development and Quality Control. 2000, Aspen Publishers, ISBN 0-8342-1642-6.

\* cited by examiner

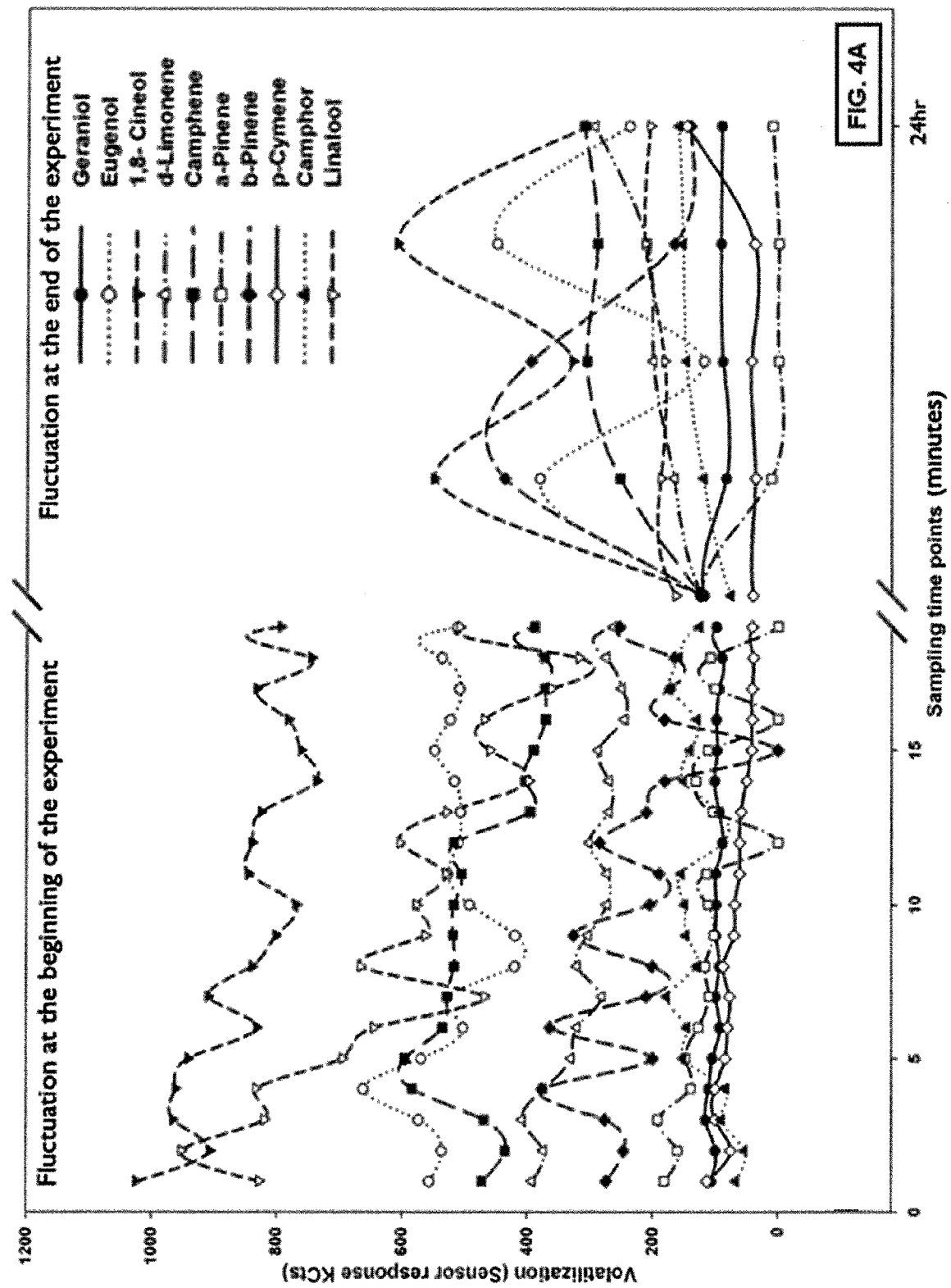

APPARATUS AND METHOD FOR CONTROLLED RELEASE OF BOTANICAL FUMIGANT PESTICIDES

CROSS-REFERENCE TO RELATED APPLICATIONS

This application claims the benefit of U.S. Provisional Application No. 61/623,829, entitled "Apparatus and Method for Controlled Release of Botanical Fumigant Pesticides" and filed on Apr. 13, 2012. The complete disclosure of said provisional patent application is hereby incorporated by reference.

STATEMENT REGARDING FEDERALLY SPONSORED RESEARCH OR DEVELOPMENT

Not applicable

BACKGROUND OF THE INVENTION

1. Field of the Invention

The present invention relates generally to botanical fumigant pesticides and, more specifically, to a botanical fumigant pesticide composition of matter made of plant essential oils containing secondary metabolites, and an apparatus and method for the controlled release of the botanical fumigant pesticide composition of matter.

2. Brief Description of the Related Art

Pests are undeniably a part of our life. Many pests are vectors of diseases and some are even deadly. With globalization and increased international travels, pests can easily disperse. Most pest control products focus on suppressing or eliminating the pest population once they are established with little attention to dispersal prevention.

Synthetic chemical pesticides have been globally used for pest control in the past few decades and, while they provided effective control, their widespread use have led to detrimental effects on human, animals and environment. Several pesticides have been proven to leave toxic, carcinogenic and harmful persistent residues in food, soil, ground water and the environment that can negatively affect humans, domestic animals, pollinators, birds and/or fish. Moreover, after many years of exposure, some pests can develop resistance to certain synthetic pesticides and gradually render them ineffective. In fact, regulatory guidelines in many countries have restricted the use of certain synthetic harmful pesticides. As a result of these regulatory restrictions, safe, effective and economical pest management has become a significant initiative.

In recent years, many new efforts have produced potentially less dangerous pesticides, many of which use botanicals as active ingredients, acting alone or in concert with conventional synthetic pesticides. Plant essential oils within the botanical category are of great interest as a safe alternative to synthetic pesticides due to their natural origin and toxicity. Derived from plants, many of them are considered safe to humans, animals and the environment. These essential oils have been used traditionally as healing medicines in many countries and ancient people were also aware of their pesticidal properties. However, only in recent years have these oils been commercialized as pest control products. Botanical biopesticides have several modes of action and act as toxins affecting a variety of receptors found in arthropods, for example, tyramine receptors (Ennan 2005), Octopamine receptors (Ennan 2001), GABA receptors (Priestly et al. 2009) and Acetylcholine receptors (Cavanagh et al. 2002). Many of the botanical essential oils tested on insects to date appear to have multiple modes-of-action and sites-of-action in the insect nervous system and elsewhere Osman et al. 2011). With rare exceptions, most botanical essential oils are non-toxic to humans and pets.

Plant essential oils are classified as plants' secondary metabolites and are, in general, complex mixtures of volatile and semi-volatile constituents. For instance, peppermint oil consists of several secondary metabolite constituents including menthol, menthone, methyl acetate, methofuran, isomenthone, germacrene-d, trans-sabinene hydrate and pulegone. The level of these constituents in the essential oils can vary based on the origin of the plants, the environmental conditions where the plants were grown, and the method that was used to obtain the essential oils.

Plant essential oils and their secondary metabolite constituents are readily obtained from plants utilizing simple processes including steam distillation, cold press and solvent extraction. These extraction processes and related science are applied to whole plant forms in large scale. Much of what is known from scientific studies about the pesticidal properties of these plant essential oils as contact toxicants is derived from analyses of their "whole plant" extracts. Some constituents of plant essential oils can also be obtained commercially in pure forms.

While plant essential oils and their constituents (secondary metabolites) do not have a primary role in metabolism of plants, they are valuable assets for plant defense, pollination and communication. Plant secondary metabolites are organic compounds that are not directly involved in the normal growth, development or reproduction of plants. Most plant secondary metabolites have defensive roles and plants actively use them as signaling agents. Most plants are capable of responding to changes in their surroundings and can convey precise information about their overall health status through those responses. Scientific studies (Miresmailli et al. 2012) of plant-arthropod interactions within the field of chemical ecology have revealed highly specialized processes of controlled release of synthesized combinations of a plant's secondary metabolites. These metabolites are either available as reservoirs in various parts of plants or synthesized de novo by plants when they need to use the metabolites to induce a behavior or send a signal. Many studies have looked at how plants synthesize, store, utilize and control the release of their secondary metabolites to manipulate their environment (i.e. induce repellency and attractant effects on behavior of pests and their natural predators; defend their vital organs through chemical antifeedants, etc.) (Schoonhoven et al, 2006). Most plants are capable of responding to changes in their surroundings and can convey precise information about their overall health status through those responses (Volkov et al. 2003). As an example, some plants are capable of showing the footsteps of insects crawling on their foliage (Bowen et al. 2002), while some other plants react to pest oviposition or feeding (Kessler et al., 2001). One of the well-documented responses of plants to biotic stressors is the emission of herbivore induced plant volatiles (HIPVs)—also known as info-chemicals (or semiochemicals) due to the fact that they carry some information about the status of the emitter. Plant semiochemicals (including plant secondary metabolites) can strongly affect the behavior of both predatory and herbivorous arthropods in nature and some plants are under strong selection pressure to release these volatiles. Various parts of plants, including leaves from both the abaxial and the adaxial side buds and roots, are known to emit HIPVs. The HIPVs are plant and pest-specific and the information they are conveying can change based on their composition and release rate.

When plants emit info-chemicals, they induce the desired action and behavior in the signal receiver. Some plants actively control the synthesis and release of these info-chemicals, both qualitatively and quantitatively. Many of the info-chemicals used in these plant communications are building blocks of plant essential oils (secondary metabolites). The same compounds that can trigger a behavior in one insect can kill another insect. Arthropods respond to specific mixtures of these volatile signals. Some plants are capable of actively changing the composition and release rate of their volatile chemical signals, and consequently changing the signal's intended message, and hence, the behavior or effect that is triggered.

Research performed by the inventors in biofuel crops confirms that plants actively control the composition and emission rate of the volatile organic compounds (secondary metabolites) that are emitted from different parts of their canopy. This research clearly established that these volatile signals play an important role in creating the biodiversity of arthropod communities in localized bioenergy agro-ecosystems—via both attracting and repelling specific arthropods.

Specific compositions and concentrations of botanical essential oil constituents (secondary metabolites) dictate the essential oil's specific attributes such as scent, taste, and viscosity as well as their pesticidal properties. Most of these constituents are the same low molecular weight chemicals as the volatile compounds that plants use for signaling and communication and, therefore, can easily volatilize out of the essential oils' matrix. Research performed by the inventors has shown that the presence of these constituents in a liquid mixture must be at certain levels for the efficacy of botanical essential oil-based pesticides to work as contact toxicants to control spider mites.

The tendency of pesticides based on botanical essential oils to breakdown before their full toxic effect is achieved is a known limitation for their use in applications where the environmental conditions can accelerate the breakdown process or where their application is such that pests can avoid contact while the active ingredients remain toxic. The present invention has mitigated this limitation by concentrating on inhalation toxicity where the rate of secondary metabolite volatilization is controlled.

Many pests have detoxification mechanisms with which they can break down the toxins and avoid mortality. While essential oils-based botanical pesticides have the capability of knocking down pests after short periods of exposure, the challenge is to achieve mortality by sufficiently long exposures and or higher concentrations to overcome the pests' initial adaptive strategies.

Fumigants enter the arthropod pest body through inhalation. In this case, it is not necessary for pests to come into direct contact with the pesticide in liquid form as is the case with sprays and foggers that are contact pesticides. Liquid contact toxicants can be rendered ineffective if pests manage to avoid physical contact with the liquid pesticide. If a fumigant is used inside confined spaces, the pests cannot escape from the deadly effects of the toxins in gaseous form that eventually reaches them via the air they breathe. It is impossible for the pests to build immunity to the fumigant pesticide. Several essential oils have fumigant capabilities as a result of their volatilization properties against arthropod pests. During the course of developing improved apparatuses and methods of fumigation, the inventors have found that various secondary metabolites of essential oils volatilize from the essential oil mixture at different rates. Heretofore unknown and unexpected is the ability to control differential volatilization rates of individual secondary metabolite constituents of botanical essential oils for use as fumigant pesticides, as opposed to controlling the breakdown rate of the essential oils as a liquid mixture when such mixtures are used as contact pesticides. The current invention controls volatilization rates and composition of secondary metabolite constituents of botanical essential oil-based pesticides in the air to achieve the durational toxicity and concentration needed for complete mortality of target pests in contained spaces and a very effective repellant where the space is not sufficiently contained.

In recent years, several technologies and concepts have been developed to control the release of pesticides and synergize their effect via special composition of active ingredients. These technologies, such as micro-encapsulation and pellet infusion, are designed to extend the release of pesticides in the air, water or other mediums. Extended release or synergy in these products is typically measured as a quantity with respect to concentrations of the active ingredients in their mixtures (e.g. a pesticide consisting of three essential oils), or quality with respect to specific blend of active ingredients in the mixture (e.g. mixing three different essential oils at different concentration) without measuring the durational persistence of individual constituents of each active ingredient (e.g. menthol and menthon in peppermint oil) that play fundamental roles in the active ingredient chemical, physical and biological attributes and consequently the efficacy of the pesticidal mixture. The present research revealed a heretofore unknown and unexpected significant improvement in the efficacy of botanical essential oil-based pesticide mixtures as fumigants achieved by focusing on controlling release at the level of individual secondary metabolite constituents that makeup essential oils used as active ingredients, rather than the more aggregate level of whole essential oils or whole mixture of essential oils. The current invention uses novel techniques for composing, fortifying and releasing toxic secondary metabolites to assure a sustained and efficacious toxicity level of individual active ingredients in essential oil-based fumigant pesticides and constituents thereof when used in gaseous form. An equally important aspect of the current invention disclosed herein is a method of controlling volatilization, which is inspired by plants' physiological, and biochemical defensive responses. The bio-inspired method allows consistent bioactivity of released volatiles of various essential oils listed on the United States Environmental Protection Agency's (EPA) 25(b) list and 4(a) list under the Federal Insecticide, Fungicide, and Rodenticide Act (FIFRA) when used a fumigant pesticides.

The present invention is designed to emulate the function of plants' info-chemical communication processes to control volatilization rates of specific secondary metabolites to achieve pesticidal effects. The present invention is intended to mimic the natural defensive mechanism of plants by acting via four distinct phases: (1) Initiation-Once exposed to air, the secondary metabolite compounds start volatilizing from the source and over a short time period they reach a certain volatilization rate and concentration that is sufficient to cause behavioral impacts if inhaled by the pests. (2) Repellence—At this phase, more volatiles are introduced into the air at levels sufficient enough to repel the pests which causes them to move away from the source of the formula. Pests naturally move as far as they can go from the source of chemicals. In the context of a moving box if the apparatus is placed inside the box on top of the content of the box, the pests will move towards the bottom of the box. Published scientific research and inventors' laboratory observations indicate that pests never move towards the source of chemicals. (3) Knockdown—At this phase, pests will be knocked-down and become immobile. The fumigant pesticide formula is a neurotoxin and, at very low concentrations, paralyzes the pests. At this stage, pests, though still alive, are located usually far from the source of toxic formula. The pests exhibit some mechano-reactions (e.g. shaking legs, shaking antenna) such that they are completely immobile but still breathing. (4) Confirm kill—At this phase, due to prolonged exposure to toxic volatiles and accumulation of volatile toxins in their body via breathing formula infused (toxic) air, the pests die.

The present invention, uses a complex array of multiple active components with different modes of action but a single mode of entry (e.g. inhalation). As a result, the detoxification mechanisms of pests cannot remove the respective toxins fast enough to revive themselves. The trade-off between detoxification of multiple toxins and keeping the vital organs alive is so high that the pest dies within a short period of time. It is important to note that pests will be repelled and paralyzed very quickly with minute concentrations of the fumigant but the "confirm kill" time may vary relative to the exposure time that is necessary to accumulate sufficient toxic materials inside the insect body via breathing. The accumulation time is correlated to the concentration of material in the airspace. It might take longer to kill "knocked-down" pests where the concentration of the material in the air is low (as a function of space volume). However, during this time, the pests will still be immobile and accumulating the toxic materials. Changes in the concentration of toxic fumigant materials in the airspace will not stop the killing process, rather it simply delays it. The process will continue as long as the toxic materials are infused in the air.

Volatilization research in pheromones, repellents and deterrents mostly focuses on the behavior that these compounds induce in the receiver (arthropods). Technologies used in these research areas (i.e. olfactometer, electroantennogram, etc.) correlate presence and level of certain volatiles to a measurable response in the target receiver. In these cases, the behavioral response is at the center of attention and the chemicals are used mainly to reproduce those behavioral responses. Materials are typically applied to a perfumery stick and placed in a device over which an air column can flow. The repellency or attractant result on target insects is then measured. However, these test methods cannot directly measure the amounts of volatilized material that is released from the liquid or solid form. They can only measure the weight of the material before and after to infer an amount theoretically volatilized, which is subject to error depending upon the sensitivity of the material to moisture uptake over the course of the testing process. The present invention allows fine-tuning the formula based on direct measurements of volatilization.

Another area of science related to volatilization research is trace gas analysis in atmospheric chemistry, air quality and global change studies. Several technologies are used to detect and monitor levels of specific gases in the air (i.e. Proton Transfer Reaction—Mass Spectrometer (PTR-MS)) that enables researchers to monitor specific compounds. This is a global inter-continental air quality measurement technology that is not applicable to the insect-pesticide world. In all these scientific endeavors, volatilization analysis is used either as an indicator of a substance's presence in liquid or solid form (as source of the volatile), thus confirmation of an induced behavior due to that substance presence in air or monitoring level of specific chemicals. Especially in the case of fumigant toxicity and repellent effects of volatiles, there is a gap of knowledge in understanding the behavior of volatile components when they transform from liquid form to gas form. Current methods enable researchers to determine the level of these components in liquid form (e.g. Gas Chromatograph-Mass Spectrometer (GCMS), Liquid Chromatograph-Mass Spectrometer (LCMS), High Performance Liquid Chromatography (HPLC)) and they can also record the ultimate effect (mortality, repellency, etc.) yet they cannot explain the specific relationship between these components in gaseous form and how these relationships might affect the final results.

The limitations of the prior art are overcome by the present invention as described below. The present invention focuses on this unexplored area using precision analytical methods to monitor temporal and special behavior of essential oils' secondary metabolite components in gaseous form and correlate that to their bio-impact on the test subjects over time. These novel methods and better understanding of the essential oils and their micro-components behavior in gaseous form has enabled the inventors to devise proprietary methods of controlling volatile compounds' action and manipulating their impact.

This unique methodology and invention allows the presented techniques/processes to scale predictably across a variety of enclosed man-made spaces and as such creates a new, efficient and effective pest control methodology. Plants' physiological structures for storing, mixing, and resource-conserving release methods provided a bio-inspiration for our invention. The present invention relies on the fundamental sciences of insect-plant interaction and plant info-chemical communication mechanisms to design environmentally safe, sustainable and efficacious pesticide products.

BRIEF SUMMARY OF THE INVENTION

The present invention is directed to a botanical fumigant pesticide. The present invention is also directed to a method of composing a botanical fumigant pesticide comprising a mixture of a base formula and an enhancement formula. The present invention is further directed to a method for the controlled release of the botanical fumigant pesticide composition. The present invention is also directed to a method for delivering the botanical fumigant pesticide composition in a confined space such that it provides consistent bioactivity for a specific duration.

More specifically, the present invention relates to a method for ensuring bio-availability of pesticidally effective botanical essential oil-based secondary metabolites in confined spaces. In another aspect, the present invention relates to a novel bioassay methods for monitoring spatial and temporal changes in volatilization and emission of botanical essential oil secondary metabolites. In another aspect, the invention relates to methods for controlling volatilization of known minimum risk botanical pesticide active ingredients. In a related aspect, the present invention is inspired by known chemical ecology processes, such as plant chemical communication mechanisms, to achieve fumigant pesticidal efficacy. In another aspect, the present invention relates to methods of composing minimum risk botanical pesticides to assure consistent quantities and qualities of selected botanical essential oil secondary metabolites in the final product's active ingredient mixtures in gaseous form. In another aspect, the present invention relates to methods of controlling urban, apicultural, agricultural and medical arthropod pests using minimum risk botanical essential oil-based active ingredients as a fumigant.

The present invention provides a method of killing or controlling common urban, apiculture, agriculture and medical arthropod pests in enclosed spaces, which include, but are not limited to, moving boxes, moving trucks, storage containers, suitcases and baggage, closed containers, closets, drawers, pantries, attics, bee hives, pollinator nests and other confined and closed spaces. Specifically, the present invention provides a method of releasing into the enclosed spaces a consistent amount of effective pesticidal fumigant composition comprising botanical essential oil secondary metabolites for a duration long enough to achieve the pesticidal effects. The present invention also discloses a method of controlling volatilization to achieve the release of a consistent amount of botanical essential oil secondary metabolites into the enclosed space over a duration long enough to achieve arthropod pest mortality. The present invention also provides a method of product formulation that ensures a continuous and consistent level of minimum risk pesticidal botanical essential oil secondary metabolites within the enclosed and confined target spaces. The present invention is a method of controlling pests using minimum risk pesticidal botanical essential oils in a gaseous form. It is an object of the present invention to have no toxic effects on non-arthropod species achieved by exclusive use of botanical essential oils that appear on the EPA's approved list of minimum risk pesticides under Section 25(b) of the Federal Insecticide, Fungicide, and Rodenticide Act (FIFRA) and exclusive use of the associated list of safe inert ingredients.

A primary object of the present invention is to provide new methods of controlling urban pests (including, but not limited to, cockroaches, ants, silverfish, book lice and houseflies), apicultural pests (including, but not limited to, small hive beetles and varroa mites), agricultural pests (including, but not limited to, cabbage loopers, green peach aphids and two spotted spider mites), medical pests (including, but not limited to, mosquitoes, bedbugs and spiders) and indoor plant pests (including, but not limited to, spider mites and aphids) in confined spaces using botanical essential oil-based pesticides acting as fumigants.

Another object of the present invention is to provide novel bioassay methods for monitoring spatial and temporal changes in volatilization and emission of botanical essential oil secondary metabolites and controlling the volatilization characteristics of botanical essential oils to achieve consistent pesticidal efficacy over a duration long enough to kill target arthropod pests in the confined spaces.

A further object of the present invention is to provide novel method of composing a blend of botanical essential oil-based pesticidal fumigant mixture that compensate for differential volatilization rates of individual secondary metabolites of each active ingredient used in a given mixture utilizing compositional techniques developed to deliberately adjust the level of certain volatile constituents of the essential oils used as active ingredients in the pesticidal mixture.

Another object of the present invention is to provide a method of controlling urban, apicultural, agricultural and medical pests using gaseous forms of botanical essential oil-based pesticidal fumigant mixture.

An additional object of the present invention is to compose a pesticidal fumigant mixture exclusively from the EPA's FIFRA minimum risk pesticides 25(b) list.

A further object of the present invention is to provide a method of controlling arthropod pests using botanical essential oil-based pesticidal fumigant mixture within 24 hours or less.

It is another object of the present invention to provide a botanical essential oil-based pesticidal fumigant mixture in a vessel or carrier that is biodegradable.

It is still another object of the present invention to provide a method of controlling urban, apicultural, agricultural and medical arthropod pests in confined spaces using a pesticidal fumigant mixture based on botanical essential oils that has no malodorous residue.

It is yet another object of the present invention to provide a method of controlling urban, apicultural, agricultural and medical arthropod pests in confined spaces using a pesticidal fumigant mixture based on botanical essential oils that can be applied without burdensome safety precautions.

As used herein, "botanical pesticide" can mean any mixture of any essential oils listed on the FIFRA 25(b) list and any inert material listed on FIFRA 4(a) list. Botanical pesticides can be used as a contact toxicant, fumigant toxicant or anti-feedant.

As used herein, "plant essential oils" or "essential oils" can mean botanical materials derived from plants via different extraction methods. When used in botanical pesticide mixtures, essential oils are considered "active ingredients" in the botanical pesticide composition.

As used herein, "essential oils' constituents" or "secondary plant metabolites" or "volatile compounds" can mean low molecular weight chemicals that make up essential oils as complex mixtures. These chemicals and their specific composition define chemical, physical and biological attributes of essential oils such as smell, color and toxicity.

As used herein, "mode of action" or "method of killing" refers to several classes of receptors in an arthropod body (e.g. GABA, nACh, Octopamine, etc.) where secondary plant metabolites can act as inhibitors and through which they can kill the pest.

As used herein, "mode of entry" or "method of toxicity" may refer to several ways by which toxic materials enter arthropod body (e.g. direct contact, residual contact, digestion and inhalation). In the current invention, "mode of entry" or "method of toxicity" only refers to inhalation.

As used herein, "volatilization control" and "release rate control" only refer to individual "constituents" or "secondary plant metabolites" or "volatile compounds". In other contexts, "Volatilization control" and "release rate control" may refer to "botanical pesticides" as a complex mixture of essential oils.

As used herein, "pesticide" or "fumigant" or "botanical fumigant" can mean any mixture of exclusively essential oils listed on FIFRA 25(b) list and exclusively inert material listed on FIFRA 4(a) list that kill or repel target pests in confined spaces in gaseous form without direct physical contact with the target pest in liquid form.

As used herein, "pest" can mean any arthropod organism whose control is desired. Pests can include, but is not limited to, Hexapoda (e.g. Lepidoptera, Coleoptera, and Hymenoptera) and Arachnids (e.g. Acari and Aranea) that have at least one pair of spiracles that allow fumigant pesticide to enter the pest body in gaseous form.

Additional objects will be set forth, in part, in the detailed description of preferred embodiments that follows. It is to be understood that the preceding summary description and following detailed description intended only to exemplify and explain the invention and not to be viewed as restricting the invention as claimed.

These and other features, objects and advantages of the present invention will become better understood from a consideration of the following detailed description of the preferred embodiments and appended claims in conjunction with the drawings as described following:

BRIEF DESCRIPTION OF THE DRAWINGS

FIG. 4A is a graph showing the volatilization rate of various compounds in the fumigant pesticide composition of the present invention.

DETAILED DESCRIPTION OF THE INVENTION

Figure 1:
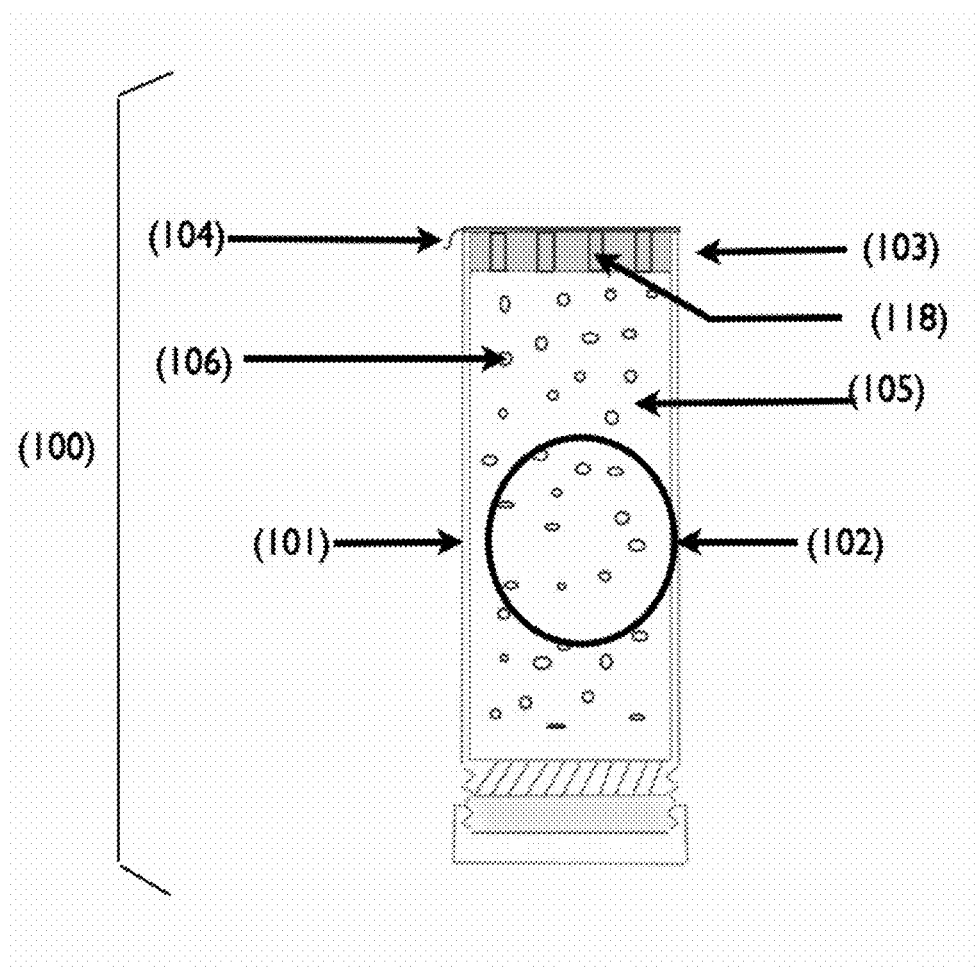
FIG. 1 is a schematic of the apparatus of the first preferred embodiment of the present invention.

With reference to FIGS. 1-6, the preferred embodiments of the present invention may be described. The fumigant pesticide composition 102 of the present invention is comprised of a base formula 105 and an enhancement formula 106. The base formula 105 and the enhancement formula 106 are mixed to form the fumigant pesticide composition 102. The base formula 105 is comprised of at least one of the botanical essential oil-based active ingredients identified under FIFRA 25(b) and at least one of the inert materials which have uniform gelatinous qualities. The mixture of the active ingredient(s) and inert material(s) forms a volatile gelatinous dispersion vehicle. The effective concentration of the active ingredient and the inert material used to form the base formula 105 is variable depending on the application, however, 45-50% active ingredient and 50-55% inert material is preferable for forming the base formula 105.

The enhancement formula 106 is comprised of at least one of the botanical essential oil-based active ingredients identified under FIFRA 25(b) and at least one of the inert materials, which may have uniform liquid or gelatinous qualities. The mixture of the active ingredient(s) and inert material(s) forms a volatile liquid or gelatinous dispersion vehicle. The effective concentration of the active ingredient and the inert material used to form the enhancement formula is variable depending on the application, however, 50-55% active ingredient and 45-50% inert material is preferable for forming the enhancement formula.

The enhancement formula 106 is blended with the base formula 105 to form a variably dense volatile fumigant pesticide composition 102. The effective amount of the fumigant pesticide composition 102 is variable depending on the application.

The botanical essential oil-based active ingredients of the present invention are chosen from the FIFRA 25(b) list known as minimum risk pesticides and includes: castor oil, linseed oil, cedar oil, malic acid, cinnamon and cinnamon oil, mint and mint oil, citric acid, peppermint and peppermint oil, citronella and citronella oil, 2-phenethyl propionate, cloves and clove oil, potassium sorbate, corn gluten meal, putrescent whole egg solids, corn oil, rosemary and rosemary oil, cottonseed oil, Sesame (includes ground sesame plant) and sesame oil, dried blood, sodium chloride, eugenol, sodium lauryl sulfate, garlic and garlic oil, soybean oil, geraniol, thyme and thyme oil, geranium oil, white pepper, lauryl sulfate, zinc metal strips (consisting solely of zinc metal and impurities), and lemongrass oil. Products solely containing the active ingredients listed in the FIFRA 25(b) list and the associated list of safe inert ingredients are exempt from federal registration. In the present invention, active and inert materials are exclusively selected from the exempt list 25(b) presented here. Therefore, as used in the claims, "essential oil-based active ingredient" and "inert material" specifically refer to and are limited to the lists of active ingredients and inert materials provided herein.

The active ingredients are selected based on their efficacy in gaseous form against individual and mixed groups of different pest species in laboratory and field experiments. Specially preferred are the active ingredients that are composed of multiple constituents including, but not limited to, castor oil, linseed oil, cedar oil, cinnamon and cinnamon oil, mint and mint oil, peppermint and peppermint oil, citronella and citronella oil, cloves and clove oil, rosemary and rosemary oil, cottonseed oil, sesame (includes ground sesame plant) and sesame oil, eugenol, garlic and garlic oil, geraniol, thyme and thyme oil, geranium oil, white pepper and lemongrass oil. The selection of active ingredients is not based on or limited to their specific mode of action (MoA) or that of their constituents' MoA. The active ingredients and their constituents might act as acetylcholinesterase (AChE) inhibitors, GABA-gated chloride channel antagonists, sodium channel modulators, nicotinic acetylcholine receptor (nAChR) agonists, nicotinic acetylcholine receptor (nAChR) allosteric modulators, chloride channel activators, selective homopteran feeding blockers, nicotinic acetylcholine receptor (nAChR) channel blockers, octopamine receptor agonists, voltage-dependent sodium channel blockers, ryanodine receptor modulators, juvenile hormone mimics, mite growth inhibitors, inhibitors of chitin biosynthesis-type 0, inhibitors of chitin biosynthesis-type 1, moulting disruptor-Dipteran, ecdysone receptor agonists, inhibitors of acetyl CoA carboxylase, inhibitors of mitochondrial ATP synthase, uncouplers of oxidative phosphorylation via disruption of the proton gradient, mitochondrial complex III electron transport inhibitors, mitochondrial complex I electron transport inhibitors, mitochondrial complex IV electron transport inhibitors, mitochondrial complex II electron transport inhibitors or miscellaneous non-specific (multi-site) inhibitors.

The inert materials used in the present invention are chosen from FIFRA 25(b) associated list of safe inert ingredients: Acetyl tributyl citrate [Citric acid, 2-(acetyloxy)-, tributyl ester]; Agar; Almond hulls; Almond shells; alpha-Cyclodextrin; Aluminatesilicate; Aluminum magnesium silicate [Silicic acid, aluminum magnesium salt]; Aluminum potassium sodium silicate [Silicic acid, aluminum potassium sodium salt]; Aluminum silicate; Aluminum sodium silicate [Silicic acid, aluminum sodium salt]; Aluminum sodium silicate (1:1:1) [Silicic acid ($H_4SiO_4$), aluminum sodium salt (1:1:1)]; Ammonium benzoate[Benzoic acid, ammonium salt]; Ammonium stearate [Octadecanoic acid, ammonium salt]; Amylopectin, acid-hydrolyzed, 1-octenylbutanedioate; Amylopectin, hydrogen 1 octadecenylbutanedioate; Animal glue; Ascorbyl palmitate; Attapulgite-type clay; Beeswax; Bentonite; Bentonite, sodian; beta- Cyclodextrin; Bone meal; Bran; Bread crumbs; (+)-Butyl lactate[Lactic acid, n-butyl ester, (S)]; Butyl lactate[Lactic acid, n-butyl ester]; Butyl stearate [Octadecanoic acid, butyl ester]; Calcareous shale; Calcite (Ca(Co3)); Calcium acetate; Calcium acetate monohydrate[Acetic acid, calcium salt, monohydrate]; Calcium benzoate[Benzoic acid, calcium salt]; Calcium carbonate; Calcium citrate[Citric acid, calcium salt]; Calcium octanoate; Calcium oxide silicate (Ca3O(SiO4)); Calcium silicate [Silicic acid, calcium salt]; Calcium stearate [Octadecanoic acid, calcium salt]; Calcium sulfate; Calcium sulfate dehydrate; Calcium sulfate hemihydrate; Canary seed; Carbon; Carbon dioxide; Carboxymethyl cellulose [Cellulose, carboxymethyl ether]; Cardboard; Carnauba wax; Carob gum [Locust bean gum]; Carrageenan; Caseins; Castor oil; Castor oil, hydrogenated; Cat food; Cellulose; Cellulose acetate; Cellulose, mixture with cellulose carboxymethyl ether, sodium salt; Cellulose, pulp; Cellulose, regenerated; Cheese; Chlorophyll a; Chlorophyll b; Citrus meal; Citric acid; Citric acid, monohydrate; Citrus pectin; Citrus pulp; Clam shells; Cocoa; Cocoa shell flour; Cocoa shells; Cod-liver oil; Coffee grounds; Cookies; Cork Corn cobs; Cotton; Cottonseed meal; Cracked wheat; Decanoic acid, monoester with 1,2,3-propanetriol; Dextrins; Diglyceryl monooleate [9-Octadecenoic acid, ester with 1,2,3-propanetriol]; Diglyceryl monostearate[9-Octadecanoic acid, monoester with oxybis(propanediol)]; Dilaurin [Dodecanoic acid, diester with 1,2,3-propanetriol]; Dipalmitin [Hexadecanoic acid, diester with 1,2,3-propanetriol]; Dipotassium citrate[Citric acid, dipotassium salt]; Disodium citrate [Citric acid, disodium salt]; Disodium sulfate decahydrate; Diatomaceous earth (less than 1% crystalline silica) [Kieselguhr; Diatomite]; Dodecanoic acid, monoester with 1,2,3-propanetriol; Dolomite; Douglas fir bark; Egg shells; Eggs; (+)-Ethyl lactate [Lactic acid, ethyl ester, (S)]; Ethyl lactate [Lactic acid, ethyl ester]; Feldspar; Fish meal; Fish oil (not conforming to 40 CFR 1040.950); Fuller's earth; Fumaric acid; gamma-Cyclodextrin; Gelatins; Gellan gum; Glue (as depolymd. animal collagen); Glycerin [1,2,3-Propanetriol]; Glycerol monooleate [9-Octadecenoic acid (Z)—, 2,3-dihydroxypropyl ester]; Glyceryl dicaprylate [Octanoic acid, diester with 1,2,3-propanetriol]; Glyceryl dimyristate [Tetradecanoic acid, diester with 1,2,3-propanetriol]; Glyceryl dioleate [9-Octadecenoic acid (9Z)—, diester with 1,2,3-propanetriol]; Glyceryl distearate; Glyceryl monomyristate [Tetradecanoic acid, monoester with 1,2,3-propanetriol]; Glyceryl monooctanoate [Octanoic acid, monoester with 1,2,3-propanetriol]; Glyceryl monooleate [9-Octadecenoic acid (9Z)—, monoester with 1,2,3-propanetriol]; Glyceryl monostearate [Octadecanoic acid, monoester with 1,2,3-propanetriol]; Glyceryl stearate [Octadecanoic acid, ester with 1,2,3-propanetriol]; Granite; Graphite; Guar gum; Gum Arabic; Gum tragacanth; Gypsum; Hematite (Fe2O3); Humic acid; Hydrogenated cottonseed oil; Hydrogenated rapeseed oil; Hydrogenated soybean oil; Hydroxyethyl cellulose[Cellulose, 2-hydroxyethyl ether]; Hydroxypropyl cellulose[Cellulose, 2-hydroxypropyl ether]; Hydroxypropyl methyl cellulose [Cellulose, 2-hydroxypropyl methyl ether]; Iron magnesium oxide (Fe2MgO4); Iron oxide (Fe2O3); Iron oxide (Fe2O3), hydrate; Iron oxide (Fe3O4); Iron oxide (FeO); Isopropyl alcohol[2-Propanol]; Isopropyl myristate; Kaolin; Lactose; Lactose monohydrate; Lanolin; Latex rubber; Lauric acid; Lecithins; Licorice extract; Lime (chemical) dolomitic; Limestone; Linseed oil; Magnesium carbonate[Carbonic acid, magnesium salt (1:1)]; Magnesium benzoate; Magnesium oxide; Magnesium oxide silicate (Mg3O(Si2O5)2), monohydrate; Magnesium silicate; Magnesium silicate hydrate; Magnesium silicon oxide (Mg2Si3O8); Magnesium stearate [Octadecanoic acid, magnesium salt]; Magnesium sulfate; Magnesium sulfate heptahydrate; Malic acid; Malt extract; Malt flavor; Maltodextrin; Methylcellulose [Cellulose, methyl ether]; Mica; Mica-group minerals; Milk; Millet seed; Mineral oil (U.S.P.); Monolaurin [Dodecanoic acid, 2,3-dihydroxypropyl ester]; Monomyristin [Tetradecanoic acid, 2,3-dihydroxypropyl ester]; Monomyristin [Decanoic acid, diester with 1,2,3-propanetriol]; Monopalmitin [Hexadecanoic acid, monoester with 1,2,3-propanetriol]; Monopotassium citrate [Citric acid, monopotassium salt; Monosodium citrate[Citric acid, monosodium salt]; Montmorillonite; Myristic acid; Nepheline syenite; Nitrogen; Nutria meat; Nylon; Octanoic acid, potassium salt; Octanoic acid, sodium salt; Oils, almond Oils, wheat; Oleic acid; Oyster shells; Palm oil; Palm oil, hydrogenated; Palmitic acid [Hexadecanoic acid]; Paper; Paraffin wax; Peanut butter; Peanut shells; Peanuts; Peat moss; Pectin; Perlite; Perlite, expanded; Plaster of paris; Polyethylene; Polyglyceryl oleate; Polyglyceryl stearate; Potassium acetate [Acetic acid, potassium salt]; Potassium aluminum silicate, anhydrous; Potassium benzoate [Benzoic acid, potassium salt]; Potassium bicarbonate [Carbonic acid, monopotassium salt]; Potassium chloride; Potassium citrate[Citric acid, potassium salt]; Potassium humate [Humic acids, potassium salts]; Potassium myristate [Tetradecanoic acid, potassium salt]; Potassium oleate [9-Octadecenoic acid (9Z)—, potassium salt]; Potassium ricinoleate [9-Octadecenoic acid, 101-hydroxy-, monopotassium salt, (9Z,101R)—]; Potassium sorbate [Sorbic acid, potassium salt]; Potassium stearate [Octadecanoic acid, potassium salt]; Potassium sulfate; Potassium sulfate [Sulfuric acid, monopotassium salt]; 1,2-Propylene carbonate[1,3-Dioxolan-2-one, 4-methyl-]; Pumice; Red cabbage color (expressed from edible red cabbage heads via a pressing process using only acidified water); Red cedar chips; Red dog flour; Rubber; Sawdust; Shale; Silica, amorphous, fumed (crystalline free); Silica, amorphous, precipitated and gel; Silica (crystalline free); Silica gel; Silica gel, precipitated, crystalline-free; Silica, hydrate; Silica, vitreous; Silicic acid (H2SiO3), magnesium salt (1:1); Soap (The water soluble sodium or potassium salts of fatty acids produced by either the saponification of fats and oils, or the neutralization of fatty acid); Soapbark; Soapstone; Sodium acetate[Acetic acid, sodium salt]; Sodium alginate; Sodium benzoate [Benzoic acid, sodium salt]; Sodium bicarbonate; Sodium carboxymethyl cellulose [Cellulose, carboxymethyl ether, sodium salt]; Sodium chloride; Sodium citrate; Sodium humate [Humic acids, sodium salts]; Sodium oleate; Sodium ricinoleate [9-Octadecenoic acid, 101-hydroxy-, monosodium salt, (9Z,101R)—]; Sodium stearate [Octadecanoic acid, sodium salt]; Sodium sulfate; Sorbitol [D-glucitol]; Soy protein; Soya lecithins; Soybean hulls; Soybean meal; Soybean, flour; Stearic acid [Octadecanoic acid]; Sulfur; Syrups, hydrolyzed starch, hydrogenated; Tetragylceryl monooleate [9-Octadecenoic acid (9Z)—, monoester with tetraglycerol]; Tricalcium citrate [Citric acid, calcium salt (2:3)]; Triethyl citrate[Citric acid, triethyl ester]; Tripotassium citrate [Citric acid, tripotassium salt]; Tripotassium citrate monohydrate [Citric acid, tripotassium salt, monohydrate]; Trisodium citrate [Citric acid, trisodium salt]; Trisodium citrate dehydrate [Citric acid, trisodium salt, dehydrate]; Trisodium citrate pentahydrate [Citric acid, trisodium salt, pentahydrate]; Ultramarine blue [C.I. Pigment Blue 29]; Urea; Vanillin [Benzaldehyde, 4-hydroxy-3-methoxy-]; Vermiculite; Vinegar (maximum 8% acetic acid in solution); Vitamin C[L-Ascorbic acid]; Vitamin E; Walnut flour; Walnut shells; Wheat; Wheat flour; Wheat germ oil;

Whey; White mineral oil (petroleum); Wintergreen oil; Wollastonite (Ca(SiO3)); Wool; Xanthan gum; Yeast; Zeolites (excluding erionite (CAS Reg. No. 66733-21-9)); Zeolites, NaA; Zinc iron oxide; Zinc oxide (ZnO); Zinc stearate [Octadecanoic acid, zinc salt].

In one application, the fumigant pesticide composition 102 includes: (1) a base formula comprising 5 mL of active ingredient A (chosen from those listed in paragraph 0057); (2) an enhancement formula comprising 5 mL of active ingredient B, 0.05 mL of active ingredient C, and 0.075 mL of active ingredient D; and (3) a carrier solvent comprising 6 mL of inert ingredient A (chosen from those listed in paragraph 0059) and 0.06 mL of inert ingredient B. The term "carrier solvent" as used herein means an inert fluid material, which may be inorganic or organic and of synthetic or natural origin, with which the active ingredient is mixed or formulated to facilitate its application to confined space to be treated. It is to be understood that these amounts are approximations and can be varied within degrees by those skilled in the art and still attain effective results. Also, other substances may be used. The above-identified materials have been used satisfactorily. The fumigant pesticide may be used in confined spaces domestically, commercially, indoors, outdoors, for pests in moving boxes. The pesticide of the present invention has also been tested and found to be effective for control of German cockroach, American cockroach, bedbug, silverfish, common spider, odorous house ant, Green peach aphid, two-spotted spider mite, cabbage looper, greenhouse whitefly and flour beetle.

Figure 2:
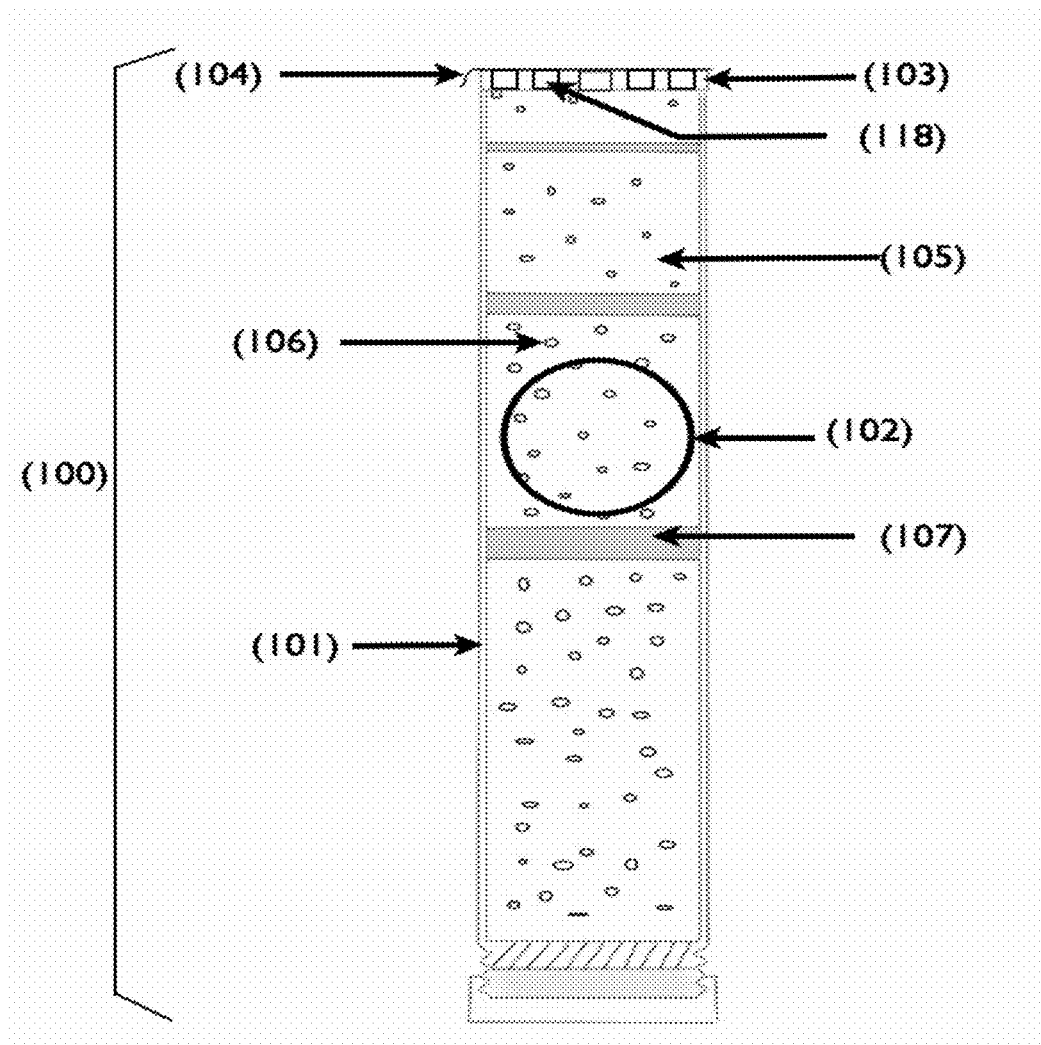
FIG. 2 is a schematic of the apparatus of the second preferred embodiment of the present invention.
Figure 3:
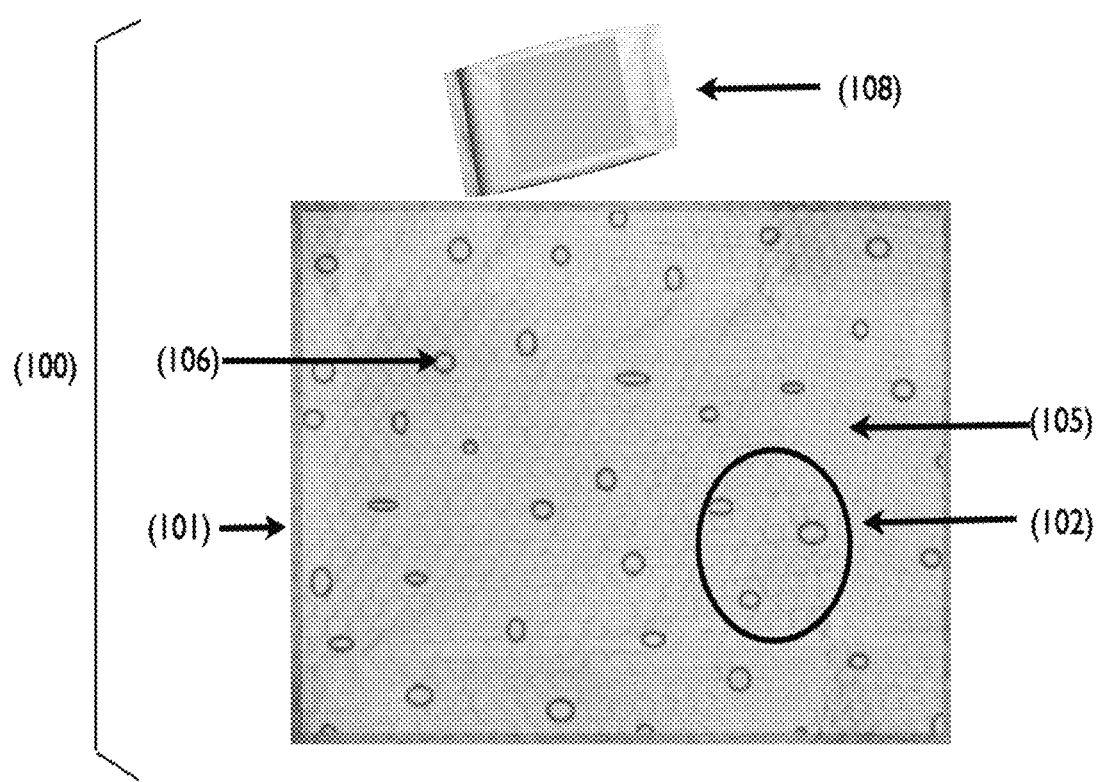
FIG. 3 is a schematic of the apparatus of the third preferred embodiment of the present invention.

The apparatus 100 of the present invention is shown in FIGS. 1-3. The apparatus comprises a carrier 101 of the fumigant pesticide composition. In one embodiment, as shown in FIGS. 1-2, the carrier 101 is a vessel that is solid, non-volatile, hollow, air-tight vessel made of biodegradable non-reactive material and is preferably cylindrical in shape. The size of the solid vessel 101 is variable depending on the application, however, the wall of the solid vessel 101 is preferably 0.5-2 mm in thickness.

In another embodiment, as shown in FIG. 3, the carrier 101 is a solid, non-volatile fibrous tissue comprising fibrous web that contains absorbent fibers. The fibrous tissue may be single-ply in which the web forming the product includes a single layer or is stratified (i.e., has multiple layers), or multi-ply, in which the webs forming the product may themselves be either single or multi-layered. Normally, the basis weight of the a fibrous tissue is less than 120 grams per square meter ("gsm"). The size of the tissue carrier 101 is variable depending on the application, however, the fibrous tissue is preferably 16 inches×16 inches and 100 gsm in weight. The carrier 101 is preferably made of materials that are biodegradable in soil, water and sunlight and meet the Biodegradable Products Institute's (BPI) certified compostable ASTM D6400 or ASTM D6868 specification without requiring high temperature conditions.

Attached at one end of the vessel carrier 101 is a release mechanism 103. The release mechanism 103 is a thin, solid, non-volatile plate made of biodegradable non-reactive material with pores such that the fumigant pesticide composition 102 cannot pass through the pores in liquid or gelatinous form, but can readily pass through in gaseous form. The pores are preferably 0.1-1 mm in size. The release mechanism 103 also comprises a cover 104 comprised of a thin, solid, non-volatile removable layer of biodegradable non-reactive material that covers the outer surface of the release mechanism 103. The cover 104 can be removed by hand and thus does not require tools or special equipment. In the second embodiment utilizing the tissue carrier, there is no separate release mechanism because the fibrous nature of the carrier acts as a release mechanism.

As described above and shown in FIG. 1, in one of the preferred embodiments, the present invention comprises a carrier 101 filled with a fumigant pesticide composition 102 comprising a base formula 105 and a enhancement formula 106. The vessel may be filled with variable amounts of the fumigant pesticide composition 102. The fumigant pesticide composition 102 is preferably comprised of 85-94% base formula 110 and 6-15% of enhancement formula 106. The vessel 101 is attached to a release mechanism 103, which is covered by a cover 104.

As shown in FIG. 2, in an alternative embodiment, the base formula 105 and the enhancement formula 106 are entrapped between one or more layers of separation formula 107. The separation formula 107 comprises at least one volatile or semi-volatile material that separates the fumigant pesticide composition 102 within the carrier 101 into two or more chambers. The volatile or semi-volatile material(s) are preferably chosen from the FIFRA 25(b) associated list of safe inert materials. The amount and thickness of separation formula 107 is variable depending on the application. The separation formula 107 protects the entrapped fumigant pesticide composition 102 beneath it from air exposure and, therefore, maintains the integrity of the fumigant pesticide composition 102. Once the fumigant pesticidal composition above the separation formula 107 is released in the air, the separation formula 107 will be exposed to air and it dissolves over time. The time it takes for the separate formula 107 to dissolve, and thus the fumigant pesticide composition 102 to disperse into the air, is dependent on the thickness of the separation formula 107. In other words, the separation formula 107 thickness determines the dispersal rate of the fumigant pesticide composition 102. As shown in FIG. 2, where multiple separation formula layers 107 are used in the apparatus 100, the thickness of the separation formula layers will decrease the closer they are positioned to the release mechanism 103. The separation formula 112 is preferably 0.2-1.5 cm in thickness.

As shown in FIG. 3, in other alternative embodiments, the fumigant pesticide composition 102 is entrapped in a carrier 101 which is a solid, non-volatile fibrous tissue comprising fibrous web that contains absorbent fibers. The fibrous tissue carrier 101 is impregnated (i.e. filled throughout or saturated) with fumigant pesticide composition 102 and is folded several times and placed inside an apparatus casing 108. The apparatus casing 108 is made of a solid, flexible, non-volatile, non-reactive, non-transparent, metalized material that is used to create a casing to protect apparatus 100. The apparatus casing 108 is vacuum-sealed to prevent air exposure. The casing 108 is non-transparent to prevent light exposure.

The present invention also provides a method for controlling urban, apiculture, agriculture and medical pests through controlled release of the botanical fumigant pesticide composition 102 from the vessel carrier 101 and controlled volatilization of plant secondary metabolites that are building blocks of active ingredients. As shown in FIGS. 1-2, this method commences by physically exposing the release mechanism 103 by removing the cover 104. The opening of the release mechanism 103 initiates a volatilization process of releasing a gaseous form of the fumigant pesticide composition 102 into the airspace of the enclosed space where the apparatus 100 is positioned. The fumigant pesticide composition 102 is comprised of both a base formula 105 and an enhancement formula 106, both of which are highly volatile. The volatilization of the composition will begin upon opening of the release mechanism 103. The essential oils' constituents (plant secondary metabolites) are highly volatile and have a great tendency to leave the mixture as means for escaping are available. The enhancement formula 106 regulates qualitative volatilization of secondary metabolites out of the fumigant pesticide formula, and consequently the composition of secondary metabolites in the air, by providing a specific arrangement and mixture of specific active ingredients and inert materials that interact with secondary metabolites of the base formula and control their volatilization. The separation formula 107 serves to control the volatilization of the fumigant pesticide composition 102. Over time, the separation formula 107 will dissolve and the fumigant pesticide composition 102 entrapped in chambers formed by the layer(s) of separation formula 107 will be volatilized in sequence. The apparatus 100 is designed such that it provides 24 hours to two months of volatilization within the enclosed space before the fumigant pesticide is completely dispersed. Residue of inert material that forms the gelatinous composition may remain inside the vessel 101 after the fumigant pesticide composition 102 is fully volatilized.

Using the tissue carrier 101 (instead of the vessel carrier 101), this method commences by physically exposing the tissue carrier 101 containing the fumigant pesticide composition 102 to air by taking the tissue carrier 101 out of the apparatus casing 108 (i.e. removing the apparatus casing 108). Exposing the fibrous tissue carrier 101 to air initiates the process of releasing a gaseous form of the fumigant pesticide formula 102 into the airspace of the enclosed space where the apparatus 100 is positioned. The fumigant pesticide composition 102 is comprised of both a base formula 105 and an enhancement formula 105, both of which are highly volatile. The volatilization of the composition will begin upon opening of the apparatus casing 108. The essential oils' constituents (plant secondary metabolites) are highly volatile and have a great tendency to leave the mixture as soon as they find a way out. The enhancement formula 106 regulates qualitative volatilization of secondary metabolites out of the fumigant pesticide formula, and consequently the composition of secondary metabolites in the air, by providing specific arrangement and mixture of specific active ingredients and specific inert materials that interact with secondary metabolites of the base formula and control their volatilization. The apparatus 100 shown in FIG. 3 is designed such that it provides 24 hours of volatilization within the enclosed space before the fumigant pesticide formula is completely dispersed.

A standard bioassay method was conducted to determine the pesticidal activity of a fumigant pesticide composition prototype consisting of several active ingredients (rosemary, thyme, wintergreen, camphor, peppermint, geraniol, and clove oil) against German cockroaches. The volatilization of the prototype of the fumigant pesticide composition was monitored inside empty moving boxes. For this standard bioassay, ten adult German cockroaches 113 were placed inside a fumigation test arena 110 with a food and water source. The arena was covered with a mesh screen 111 to prevent roaches from escaping. Ten mL of the fumigant pesticide composition prototype was placed inside a 40 mL GC vial. The vial was then placed inside a medium size moving box 109 along with the roaches 113.

An ultra-fast gas chromatograph 116 monitored the volatilization of the fumigant pesticide composition prototype from the vial 60 minutes after the box was closed. Volatile monitoring was performed at two steps. Step one started 60 minutes after the box was closed and volatile samples were collected every 5-minutes for 90 minutes. The second step started 23 hours after the box was closed and samples were collected every 5-minutes for 50 minutes. The ultra-fast gas chromatograph 116 parameters included: Sensor 80° C., Pump 5 sec, Column 40° C., Ramp 10 c/sec, Valve 165° C., Inlet 200° C. The volatilization patterns of the major constituents of fumigant pesticide composition prototype tested inside a medium size empty box are shown in FIG. 4. The first half of the graph (on the left side) shows fluctuation of volatiles at the beginning of the experiment (i.e. step one), while the second half of the graph (on the right side) shows the fluctuation of volatiles at the end of the experiment (i.e. step two).

Figure 4B:
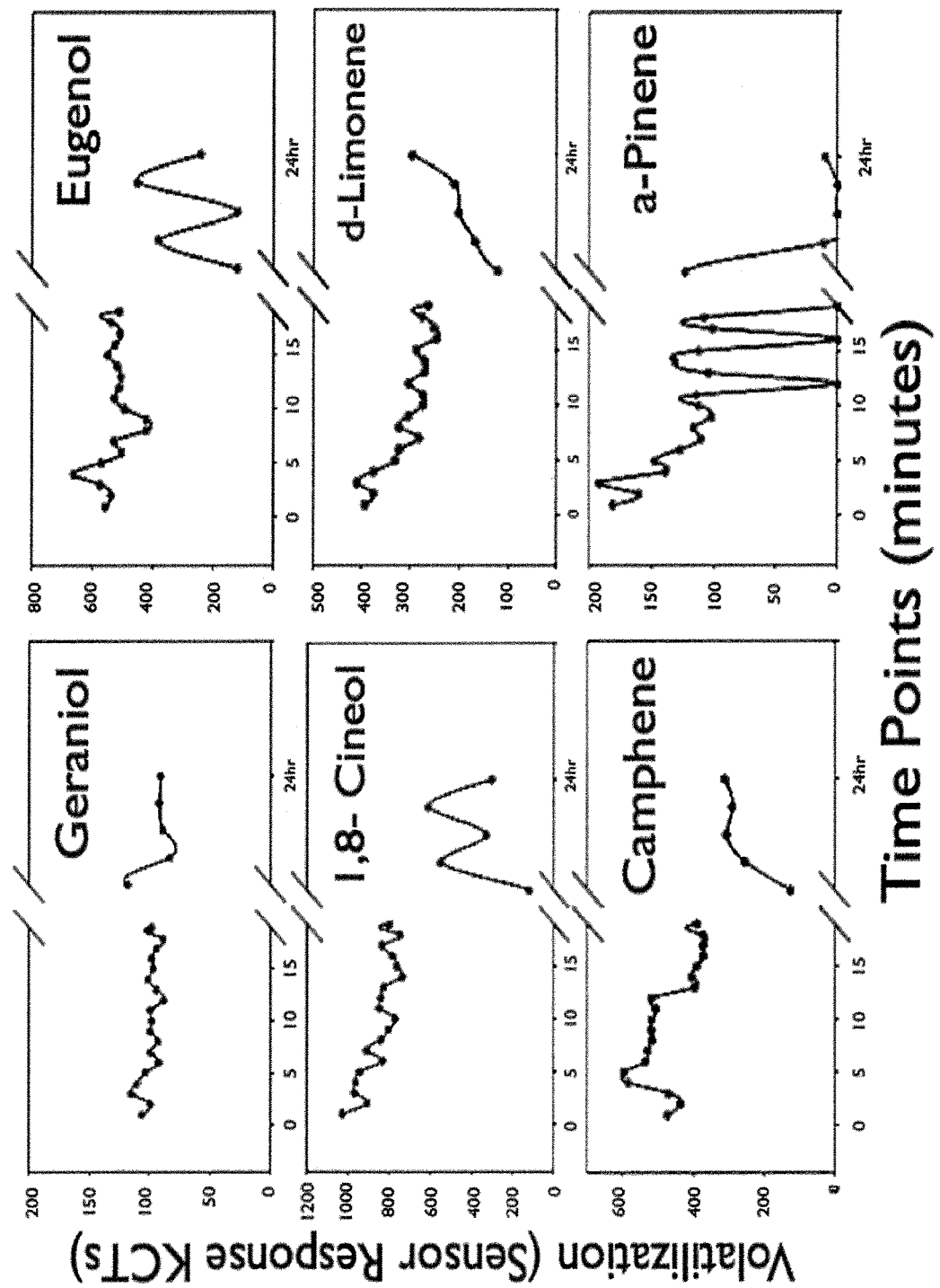
FIGS. 4B-4C are graphs showing the volatilization rate of various compounds in the fumigant pesticide composition of the present invention.
Figure 4C:
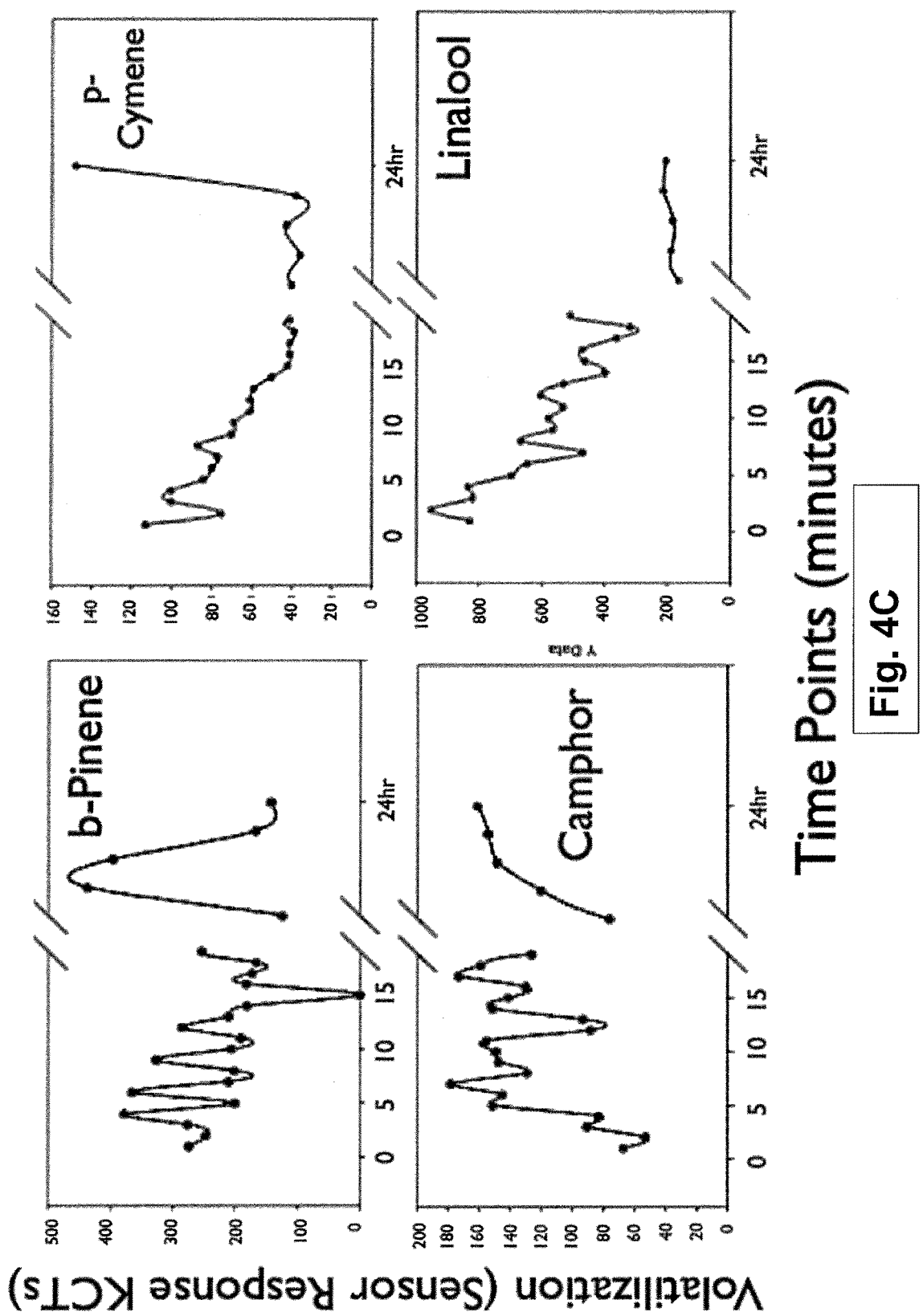
Figure 5:
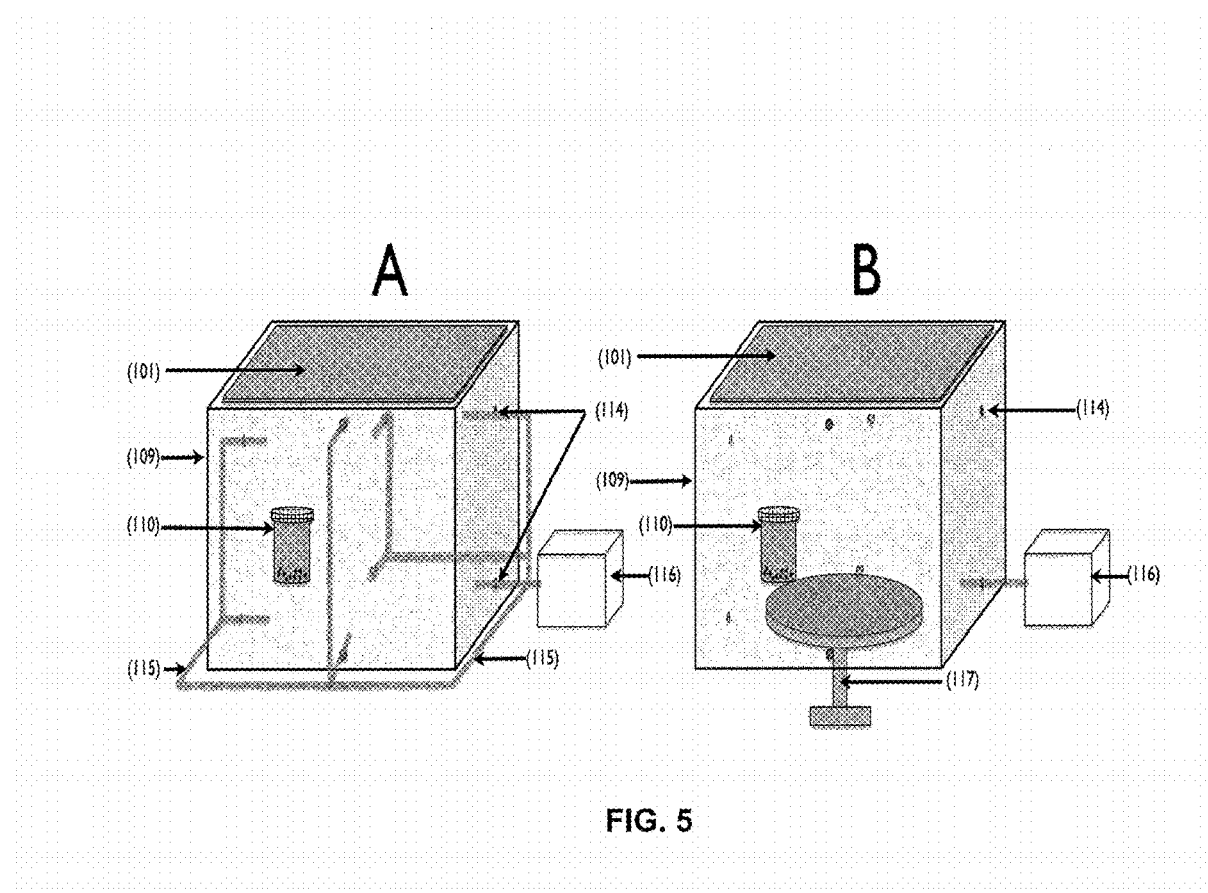
FIG. 5A is a schematic of an experimental set-up of the present invention.
FIG. 5B is a schematic of an experimental set-up of the present invention.

As shown in FIGS. 4A-4B, the results indicate that certain components (i.e. eugenol) of fumigant pesticide composition prototype inhibit volatilization of other components (i.e. alpha-pinene and beta-pinene) that are important to toxicity of the composition. A significant fluctuation was observed in the volatilization of these components from the composition and certain compounds never reached the expected full volatilization level. The level of fluctuation was lower within time periods closer to the onset of the method (time points 0-15), but it was amplified closer to the end (time point 24 hr). Some essential oils share certain secondary metabolites in their composition. For example limonene can originate from rosemary oil as well as wintergreen oil. The working assumption for this experiment was that the secondary metabolites would volatilize freely off the mixture of essential oils in the fumigant pesticide formula independent of their source. Our results clearly indicate that it is not true.

The essential oils used for the fumigant pesticide composition prototype used in this standard bioassay were a complex mixture of several constituents of which only a few major ones are important for toxicity (e.g. 1,8-Cineole, alpa-pinene, and camphor) because (1) they form the majority of the essential oil composition and (2) they have proven record of toxicity against pest. However, the impact of other minute secondary metabolites of the essential oils, such as p-Cymene, cannot be ignored as it relates to the physical act of volatilization. Although their abundance in the essential oil composition is significantly lower than the major constituents, they still are capable of forming the oil physical characteristics and manipulate volatilization of other constituents.

As shown in FIG. 4, the pattern of volatilization of each individual secondary metabolite compound that was monitored in this bioassay was separated to identify four distinct patterns of volatilization in the fumigant pesticide composition prototype:

1-Unstable pattern with greater fluctuation at the end of trial (e.g. Eugenol, 1,8-Cineole). The volatiles in this group gradually decrease over time, yet there are significant pulsing effect with continued bursts of volatiles.
2-Complete inhibition pattern (e.g. alpha-pinene and beta-pinene). In these compounds, the volatilization at some point is completely inhibited (level drops to zero) and we see big burst of compounds closer to the end of trial.
3-Fluctuation pattern with increasing levels at the tail end (e.g. d-limonene, p-cymene, camphor, and camphene). For these compounds the volatilization level increases over time.
4-Steady compounds (e.g. geraniol and linalool). These compounds either stay at relatively same level of decrease gradually over time without unexpected bursts at the end.

These patterns clearly indicate active inhibition of these secondary metabolite components in the fumigant pesticide composition prototype because the presence of these secondary metabolites in the air fluctuates over time. These results are more apparent when certain statistics are considered (in this case, max, min, mean and SD). It is clear that certain components were inhibited at the beginning of the bioassay (e.g. Linalool) yet at the end their volatilization increased significantly at the end of the trial. This explains why only 10% mortality was observed in cockroaches. Some toxic components (alpha-pinene and beta-pinene) were inhibited by the blend and were not present in the air at the toxic level.

In order to determine the adequate amount and desired composition of fumigant pesticide for effective control of pests inside a packed box, novel bioassay methods were used to measure volatilization of the composition inside packed boxes using precision analytical methods to monitor temporal and special behavior of essential oils' secondary metabolite components in gaseous form and to correlate that to their bio-impact on the test subjects over time. These novel methods and a better understanding of the essential oils and their micro-components behavior in gaseous form has enabled the inventors to devise methods of controlling the actions of volatile compounds and manipulating their impact. The novel bioassay methods consist of two volatile collection and air monitoring systems and a novel toxicity test arena as shown in FIG. 5 and FIG. 6.

The first volatile collection and monitoring system shown in FIG. 5A consists of FESTO® food grade tubes 115 that connect a moving box 109 to the ultra-fast gas chromatograph 116. In order to insure consistency of sampling, the airflow of each tube and opening was measured via a digital flow meter and proper adjustments were made. Replicated groups of ten adult cockroaches 113 from culture were confined in a test arena 110 consisting of a plastic bucket (8 cm diameter, 15 cm length) covered by a mesh screen 111 that prevent roaches from escaping the arena yet allow air circulation. Test arenas 110 were equipped with a water and food source. The boxes contained various items representing a typical moving box (e.g. books, articles of clothing, small boxes, plastic items, small kitchen utensils, wrapping paper, newspaper, etc.). A 16×16 inch fibrous tissue carrier 101 impregnated with various amounts of fumigant pesticide composition ranging from 6-12 mL was placed on top of the contents in the box prior to closing the box. In positive control groups, the fibrous tissue carrier was only impregnated with carrier solvent. In negative control groups, the fibrous tissue was not impregnated. A HOBO data logger measured relative humidity and temperature inside the box. The boxes 109 were placed on a bench at room temperature. The efficacy of the present pesticide composition was determined 24 hours after the onset of the experiment by counting cockroach knockdown and mortality in test arenas. To confirm mortality, test arenas were removed from the box 24 hours after the onset of the experiment and aerated under laminar flow hood for an additional 48 hours.

The ultra-fast gas chromatograph 116 was programmed to collect samples for 20 seconds. To eliminate background noise in the box that could potentially interfere with formula volatiles, the program was modified to ramp from 40 c to 150 c at 10 c/Sec. Volatile samples were taken every five minutes for 6 hours. At each sampling point, five tubes were manually shut off using the shut off valves, leaving only one sampling position to be active. Samples were collected from each side of the box following up-down sampling sequence. Within the five-minute window between each sampling point, the amounts of detected compounds were recorded. The volatilization data was analyzed using multivariate analysis of variance (MANOVA) using the location of sampling as fix factor, time as co-variate, and volatile amounts at each sampling point as dependent variables.

In the second volatile collection and monitoring system shown in FIG. 5B, all tubing and valves 115 were eliminated to prevent the possibility of detecting ghost peaks caused by volatile residues. In a series of experiments, the sampling time of the ultra-fast gas chromatograph 116 was reduced to 5 seconds to capture a snap shot of volatiles at each sampling point 114. It was necessary to recalibrate the ultra-fast gas chromatograph 116 and re-adjust the analytical methods using authentic standards each time a test element was modified. Resolvability of the peaks was changed and components with similar Kovat indices, such as limonene and cineole co-elute, made identification almost impossible. This issue was remedied by modifying column ramping from 10 c/sec to 9.7/sec. The ultra-fast gas chromatograph 116 was placed in a fix position and the box 109 was placed on a rotating stool 117. The position of the ultra-fast gas chromatograph 116 was adjusted so it could take a sample from each sampling point 114. Three methods for the ultra-fast gas chromatograph 116 were developed to measure three (1,8-cineole, camphor, and alpha-pinene) of ten major volatiles in different sampling points 114 in the box 109.

To monitor temperature and relative humidity inside the box, HOBO data loggers were placed inside the box. The ultra-fast gas chromatograph 116 was programmed as follows: Column initial temp: 40 c, Valve temp: 165 c, Inlet temp: 200 c, Trap temp: 250 c, Final column temp: 200 c, Ramp: 9.7 sec, Sensor temp: 80 c, Sensor bake: 30 sec at 150 c, Pump: 5 sec, Flow: 3 cc/min. To eliminate contamination, at each sampling point 114, an HPLC grade pipette tip was installed in the box through which the inventors inserted a leur lock needle for sampling. The needle was marked with a tape so it would not reach too far inside the box without the protection of HPLC tip. To eliminate possible residual contamination, in between each sample, we took an air blank sample from an empty GC vial through septa and baked the ultra-fast gas chromatograph 116 sensor and column for 30 seconds. This protocol ensured that volatile readings at each point were a true representation of the concentration at that given time and location and not a carry-over from previous samplings.

These experimental set-ups allowed the accurate measurement of the amount of each secondary metabolite emitted from the fumigant pesticide composition at any given time and location inside the confined space and allowed a better understand the behavior of individual chemicals in gaseous form inside the confined space. This data of temporal and spatial distribution and concentration of individual secondary metabolites present in the air is shown in Example 1. The novel methods of the present invention will be further illustrated in the following non-limiting examples. The examples are illustrative of various embodiments only and do not limit the claimed invention regarding the materials, conditions, concentrations, weigh ratios, process parameter and the like recited herein.

Example 1

As explained above, it was demonstrated that there exists an active inhibition among secondary metabolite components in the fumigant pesticide composition prototype. A novel bioassay method was developed to pin-point exact concentrations of individual secondary metabolites of the fumigant composition at any given time and location inside confined spaces. The interactions among individual secondary metabolites was scrutinized and their ability to inhibit each other as a solution was used to block volatilization of undesired constituents of active ingredients in the fumigant pesticide composition that do not play a role in its toxic effect against target pests. The volatilization of the important secondary metabolites, such as 1,8-cineole, was controlled at certain levels. An enhancement formula was created, which included minute amounts of certain active and inert ingredients (e.g. peppermint oil and isopropyl myristate), and added to the fumigant pesticide composition prototype to block emission of undesired volatiles (e.g. eugenol) and enhance emission of toxic components of base formula. The effectiveness of this approach was verified both by methods and blind headspace analysis of the pesticide composition prototype along with three commercial essential oil samples.

In this study, a liquid fumigant pesticide formulation was prepared as follows:

(1) Base formula: rosemary oil (5 ml)

(2) Enhancement formula: rosemary oil high quality (0.5 ml); clove oil (0.05 ml); peppermint oil (0.075 ml)

(3) Carrier solvent: isopropyl alcohol (6 ml); isopropyl myristate (0.06 ml).

Blending:

3. The required amounts of base formula ingredients were drawn from individual stocks of chemicals via a laboratory pipette and were transferred into a 40 ml GC glass vial (2.5 cm diameter by 10 cm length) with a silicon septa. The tall vial was used to minimize surface area of liquid that is exposed to the air during preparation. The chemicals were added quickly (less than 10 second to transfer each chemical) in order to minimize exposure to air. Following the same instruction, the enhancement formula was prepared and added to the same vial.

4. The carrier solvent was then poured over the base formula and enhancement formula inside the vial. The vial was closed immediately after the solvent was added. The base formula, enhancement formula and carrier solvent were mixed using a lab shaker for 15 seconds.

A sub-sample of the fumigant pesticide composition (0.5 ml) was placed inside a 1 ml GC vial. Three commercial samples of rosemary oil was also placed inside three separate 1 mL GC vials. Headspace volatilization of secondary metabolites from these four samples were compared using a gas chromatograph mass spectrometer (GCMS). The GCMS was programmed to only collect samples from the headspace above the liquid mixture of the chemicals in the vials. The sampling needle of the GCMS did not enter the liquid matrix of the samples and stayed in the headspace to collect chemicals in gaseous form inside the vials. The GCMS was a Varian 3900 system with a Saturn 2100T ion trap mass-selective detector (Varian Inc., Walnut Creek, Calif.). The inventors used a WCOT fused silica 30 m Å~0.25 mm i.d. column with a CP-Sil 8 CB low bleed MS coating (Varian Inc.), a 1 μL injection volume and pure helium as the carrier at 1.0 ml min-1. The temperature program used was 80° C. for 0.5 min, an increase of 8.0 $ Cmin-1 for 8.0 min, followed by an increase of 50° C. min-1 for 3.2 min. Cinnamic alcohol (Sigma, St Louis, Mo., USA) was used as an internal standard.

The following tables show the amount of certain secondary metabolites in headspace of three commercial essential oil samples and the fumigant pesticide composition of the present invention. As expected, by using this approach, the inventors blocked emission of some of the constituents of essential oils used in the base formula and only allowed emission of five major constituents that are toxic to wide range of target pests as shown in Table 4.

TABLE 1

Commercial rosemary oil sample one

| Secondary metabolites | Retention Time | Peak Area | % |
|---|---|---|---|
| a-pinene | 2.834 | 23036 | 6.53 |
| Camphene | 3.005 | 15051 | 4.26 |
| b-pinene | 3.259 | 28241 | 8.00 |
| p-Cymene | 3.690 | 6667 | 1.89 |
| 1,8-Cineole | 3.800 | 201357 | 57.05 |
| 3-Carene | 4.472 | 6627 | 1.88 |
| Camphor | 5.223 | 41975 | 11.89 |
| Isoborneol | 5.417 | 6137 | 1.74 |
| Borneol | 5.517 | 14325 | 4.06 |
| Bornyl Acetate | 6.912 | 9547 | 2.70 |
| Total | | 352963 | 100 |

TABLE 2

Commercial rosemary oil sample two

| Secondary metabolites | Retention Time | Peak Area | % |
|---|---|---|---|
| a-Pinene | 2.835 | 61832 | 18.15 |
| Camphene | 3.005 | 44428 | 13.04 |
| b-Pinene | 3.260 | 18501 | 5.43 |
| p-Cymene | 3.693 | 8725 | 2.56 |
| D-Limonene | 3.747 | 15901 | 4.67 |
| 1,8-Cineole | 3.806 | 73368 | 21.53 |
| Camphor | 5.229 | 86905 | 25.50 |
| Isoborneol | 5.427 | 7759 | 2.28 |
| Borneol | 5.526 | 12252 | 3.60 |
| Isopropyl acetate | 6.920 | 11088 | 3.25 |
| Total | | 340759 | 100 |

TABLE 3

Commercial rosemary oil sample three

| Secondary metabolites | Retention Time | Peak Area | % |
|---|---|---|---|
| a-Pinene | 2.839 | 49740 | 14.73 |
| Camphene | 3.007 | 33986 | 10.06 |
| b-Pinene | 3.263 | 21023 | 6.22 |
| p-Cymene | 3.696 | 6782 | 2.01 |
| Camphene | 3.749 | 15944 | 4.72 |
| 1,8-Cineole | 3.806 | 124782 | 36.95 |
| Camphor | 5.232 | 62824 | 18.60 |
| Borneol | 5.429 | 5678 | 1.68 |
| a-Terpineol | 5.778 | 8373 | 2.48 |
| Bornyl Acetate | 6.925 | 8589 | 2.54 |
| Total | | 337721 | 100 |

TABLE 4

Pesticide fumigant formula of the present invention

| Secondary metabolites | Retention Time | Peak Area | % |
|---|---|---|---|
| a-Pinene | 2.838 | 20389 | 14.58 |
| Camphene | 3.007 | 13963 | 9.98 |
| b-Pinene | 3.263 | 7486 | 5.35 |
| 1,8-Cineole | 3.875 | 65423 | 46.78 |
| Camphor | 5.232 | 32588 | 23.30 |
| Total | | 139849 | 100 |

Example 2

A study was also conducted to determine the pesticidal activity of the composition of the present invention against commonly found pests, such as German Cockroaches, Bedbugs and Odorous house ants, inside packed moving boxes.

Figure 6:
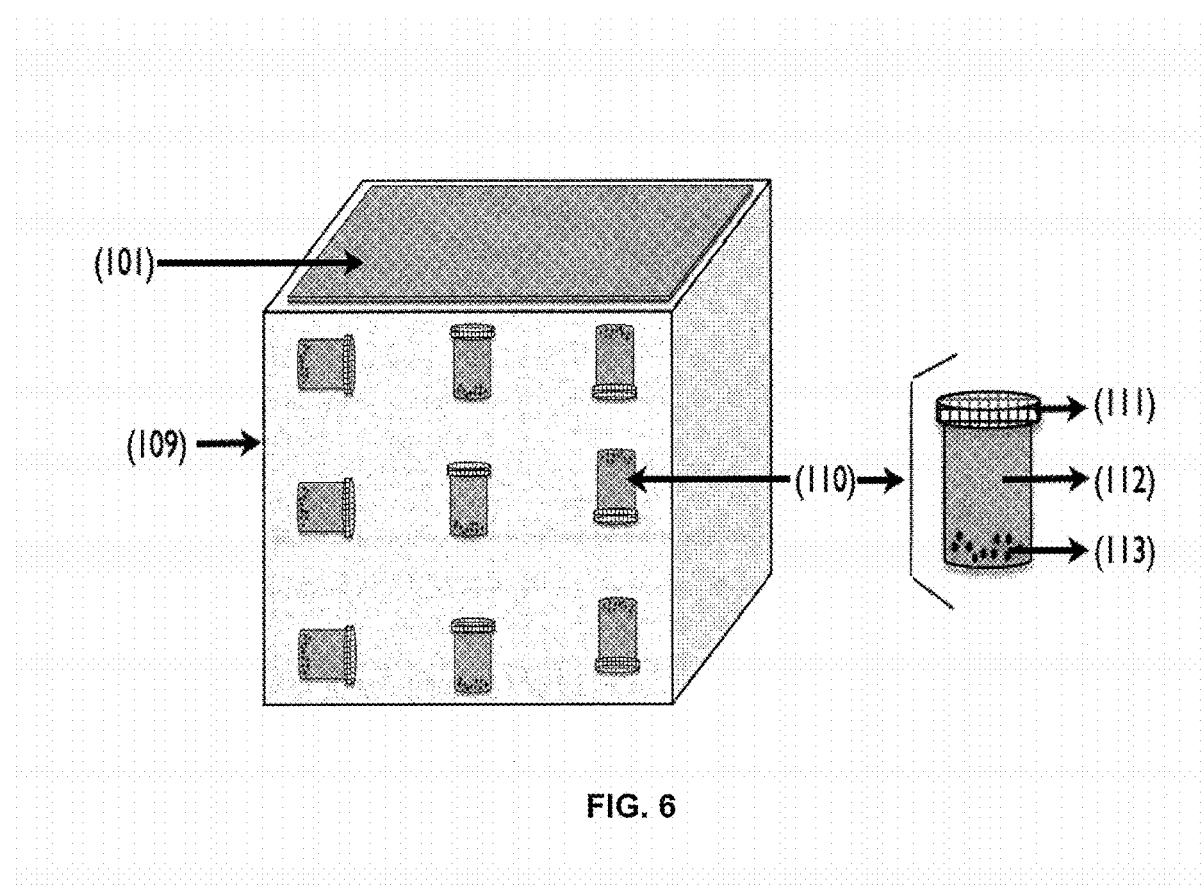
FIG. 6 is a schematic of an experimental set-up of the present invention.

The intrinsic insecticidal activity of the fumigant pesticide formula against *B. germanica* was demonstrated by exposing cockroaches to the fumigant pesticide composition used in Example 1. Replicated groups of ten adult cockroaches 113 from culture were confined in a test arena 110 consist of a plastic bucket (8 cm diameter, 15 cm length) 112 covered by a mesh screen 111 that prevent roaches from escaping the arena yet allow air circulation. Test arenas 110 were equipped with a water and food source. Nine test arenas 110 were placed inside each packed medium size moving box 109 (3 cubic foot) in different orientation and location inside the box as shown in FIG. 6. The boxes contained various items representing a typical moving box (e.g. books, articles of clothing, small boxes, plastic items, small kitchen utensils, wrapping paper, newspaper, etc.). A 16×16 inch fibrous tissue carrier 101 impregnated with 11.5 ml of fumigant pesticide formula was placed on top of the contents in the box prior to closing the box. In positive control groups, the fibrous tissue carrier was only impregnated with carrier solvent. In negative control groups, the fibrous tissue was not impregnated. A HOBO data logger measured relative humidity and temperature inside the box. The boxes 109 were placed on a bench at room temperature. The efficacy of the present pesticide invention was determined 24 hours after the onset of the experiment by counting cockroach knockdown and mortality in test arenas. To confirm mortality, test arenas were removed from the box 24 hours after the onset of the experiment and aerated under laminar flow hood for an additional 48 hours. After the aeration period, the knocked-down cockroaches inside the test arena were probed by a paintbrush. Those cockroaches that did not moved their appendages were considered dead. The efficacy of the fumigant pesticide composition was determined by counting the number of cockroaches with their mortality confirmed. The affected cockroaches had curled or distended abdomens, and looked to be paralyzed as when poisoned by a nervous system pesticide. One hundred percent mortality in all nine test arenas was achieved when 11.5 mL of fumigant pesticide composition was applied. The above experiment with cockroaches indicates that the toxicity of the fumigant pesticide composition presented here at aforementioned concentrations was not affected by the location or orientation of the test arena in the packed box, the contents of the box, or the fluctuation of the relative humidity and temperature inside the box during the course of experiment.

REFERENCES

Enan, E. E. (2005). Molecular response of *Drosophila melanogaster* tyramine receptor cascade to plant essential oils. *Insect biochemistry and molecular biology*, 35(4), 309-321.

Enan, E. (2001). Insecticidal activity of essential oils: octopaminergic sites of action. *Comparative Biochemistry and Physiology Part C: Toxicology & Pharmacology*, 130(3), 325-337.

Priestley, C. M., Williamson, E. M., Wafford, K. A., & Sattelle, D. B. (2009). Thymol, a constituent of thyme essential oil, is a positive allosteric modulator of human GABAA receptors and a homo-oligomeric GABA receptor from *Drosophila melanogaster*. *British journal of pharmacology*, 140(8), 1363-1372.

Cavanagh, H. M. A., & Wilkinson, J. M. (2002). Biological activities of lavender essential oil. *Phytotherapy Research*, 16(4), 301-308.

Isman, M. B., Miresmailli, S., & Machial, C. (2011). Commercial opportunities for pesticides based on plant essential oils in agriculture, industry and consumer products. *Phytochemistry Reviews*, 10(2), 197-204.

Volkov, A. G., Ranatunga, D. R. A. 2006. Plants as environmental biosensors. *Plant Signaling and Behavior* 1:105-115.

Miresmailli, S., Gries, R., Gries, G., Zamar, R. H. and Isman, M. B. 2012. Population density and feeding duration of cabbage looper larvae on tomato plants alter levels of plant volatile emission. *Pest Management Science*, 68: 101-107.

Schoonhoven, L. M., van Loon, J. J. A., Dicke, M. 2006. Insect-Plant Biology. New York: Oxford University Press. 421 p.

Bowen, A. W., Hall, D. E., MacGregor, K. B. 2002. Insect footsteps on leaves stimulate the accumulation of 4-aminobutyrate and can be visualized through increased chlorophyll fluorescence and superoxide production. *Plant Physiology* 129:1430-1434.

Kessler, A., Baldwin, I. T. 2001. Defensive function of herbivore-induced plant volatile emissions in nature. *Science* 291:2141-2144.

Carpenter et al. Guidelines for Sensory Analysis in Food Products Development and Quality Control. 2000, Aspen Publishers, ISBN 0-8342-1642-6

Having now fully set forth detailed examples and certain modifications incorporating the concept underlying the present invention, various other modifications will obviously occur to those skilled in the art upon becoming familiar with said underlying concept. It is to be understood therefore, that within the scope of the appended claims, the invention may be practiced otherwise that as specifically set forth herein.

Although illustrative embodiments of the invention have been described in detail, it is to be understood that the present invention is not limited to those precise embodiments, and that various changes and modifications can be effected therein by one skilled in the art without departing from the scope and spirit of the invention as defined by the appended claims.

The present invention has been described with reference to certain preferred and alternative embodiments that are intended to be exemplary only and not limiting to the full scope of the present invention as set forth in the appended claims.

We claim:

1. An apparatus for the controlled release of a pesticide composition, wherein said apparatus comprises:
   (a) a carrier; and
   (b) a pesticidal composition contained in said carrier, wherein said pesticidal composition comprises a pesticidally effective amount of a base formula and a pesticidally effective amount of an enhancement formula, wherein base formula comprises at least one essential oil-based active ingredient, wherein said essential oil-based active ingredient is comprised of a plurality of secondary metabolites, wherein said enhancement formula is effective to inhibit the release of at least one of said plurality of secondary metabolites under conditions effective for the volatilization of said pesticidal composition, wherein said enhancement formula is effective to enhance the release of at least one of said plurality of secondary metabolites under conditions effective for the volatilization of said pesticidal composition.

2. The apparatus of claim 1, wherein said carrier is a vessel carrier or a fibrous tissue carrier.

3. The apparatus of claim 2, wherein said vessel carrier comprises an open end and a closed end, wherein said vessel carrier further comprises a plate covering said open end of said vessel carrier, wherein said plate comprises pores configured to permit release of said pesticidal composition from said vessel carrier when said pesticidal composition is in a gas phase but prevent release of said pesticidal composition from said vessel carrier when said pesticidal composition is in a liquid phase.

4. The apparatus of claim 2, wherein said vessel carrier further comprises a separation formula dividing said pesticidal composition into two or more layers, wherein a composition of said separation formula is effective to control the rate of release of the pesticidal composition from said vessel carrier.

5. The apparatus of claim 4, wherein said separation formula is comprised of at least one semi-volatile or volatile inert material.

6. The apparatus of claim 2, wherein said fibrous tissue carrier is positioned in a casing, wherein said casing is comprised of a non-volatile, non-reactive, non-transparent material.

7. The apparatus of claim 1, wherein said apparatus is effective to kill pests for at least twenty-four hours.

8. The apparatus of claim 1, wherein said essential oil-based active ingredients are chosen from the list of castor oil, linseed oil, cedar oil, malic acid, cinnamon and cinnamon oil, mint and mint oil, citric acid, peppermint and peppermint oil, citronella and citronella oil, 2-phenethyl propionate, cloves and clove oil, potassium sorbate, corn gluten meal, putrescent whole egg solids, corn oil, rosemary and rosemary oil, cottonseed oil, sesame and sesame oil, dried blood, sodium chloride, eugenol, sodium lauryl sulfate, garlic and garlic oil, soybean oil, geraniol, thyme and thyme oil, geranium oil, white pepper, lauryl sulfate, zinc metal strips, and lemongrass oil.

9. An apparatus for the controlled release of a pesticide composition, wherein said apparatus comprises:

(a) a vessel carrier;
(b) a pesticidal composition contained in said vessel carrier, wherein said pesticidal composition comprises a pesticidally effective amount of a base formula and a pesticidally effective amount of an enhancement formula, wherein base formula comprises at least one essential oil-based active ingredient, wherein said essential oil-based active ingredient is comprised of a plurality of secondary metabolites, wherein said enhancement formula is effective to inhibit the release of at least one of said plurality of secondary metabolites under conditions effective for the volatilization of said pesticidal composition, wherein said enhancement formula is effective to enhance the release of at least one of said plurality of secondary metabolites under conditions effective for the volatilization of said pesticidal composition; and
(c) a separation formula dividing said pesticidal composition into two or more layers.

10. The apparatus of claim 9, wherein said vessel carrier comprises an open end and a closed end, wherein said vessel carrier further comprises a plate covering said open end of said vessel carrier, wherein said plate comprises pores configured to permit release of said pesticidal composition from said vessel carrier when said pesticidal composition is in a gas phase but prevent release of said pesticidal composition from said vessel carrier when said pesticidal composition is in a liquid phase.

11. The apparatus of claim 9, wherein said apparatus is effective to kill pests for at least twenty-four hours.

12. The apparatus of claim 9, wherein said essential oil-based active ingredients are chosen from the list of castor oil, linseed oil, cedar oil, malic acid, cinnamon and cinnamon oil, mint and mint oil, citric acid, peppermint and peppermint oil, citronella and citronella oil, 2-phenethyl propionate, cloves and clove oil, potassium sorbate, corn gluten meal, putrescent whole egg solids, corn oil, rosemary and rosemary oil, cottonseed oil, sesame and sesame oil, dried blood, sodium chloride, eugenol, sodium lauryl sulfate, garlic and garlic oil, soybean oil, geraniol, thyme and thyme oil, geranium oil, white pepper, lauryl sulfate, zinc metal strips, and lemongrass oil.

* * * * *